(12) United States Patent
Choe et al.

(10) Patent No.: US 7,183,459 B2
(45) Date of Patent: Feb. 27, 2007

(54) DWF7 MUTANTS

(75) Inventors: Sunghwa Choe, Tucson, AZ (US); Kenneth A. Feldmann, Newbury Park, CA (US)

(73) Assignee: The Arizona Board of Regents on Behalf of the University of Arizona, Tucson, AZ (US)

( * ) Notice: Subject to any disclaimer, the term of this patent is extended or adjusted under 35 U.S.C. 154(b) by 349 days.

(21) Appl. No.: 10/736,318

(22) Filed: Dec. 15, 2003

(65) Prior Publication Data

US 2004/0133948 A1 Jul. 8, 2004

Related U.S. Application Data

(62) Division of application No. 09/775,879, filed on Feb. 2, 2001, now abandoned.

(60) Provisional application No. 60/179,901, filed on Feb. 2, 2000.

(51) Int. Cl.
*C12N 15/29* (2006.01)
*C12N 15/82* (2006.01)
*C12N 15/87* (2006.01)
*A01H 5/00* (2006.01)

(52) U.S. Cl. .................. 800/298; 536/23.6; 435/320.1; 435/410; 800/287

(58) Field of Classification Search ............... 536/23.1, 536/23.6; 435/320.1, 410; 800/298, 278, 800/290
See application file for complete search history.

(56) References Cited

U.S. PATENT DOCUMENTS 5,451,514 A 9/1995 Boudet et al.

OTHER PUBLICATIONS

Choe et al (1999, The Plant Cell 11(2):207-221).*
Choe et al (1999, NCBI accession No. AF105034).*
Husselstein et al (1999, Plant Mol. Biol. 39:891-906).*
Husselstein et al (1999, NCBI Accession No. AF069468).*
Hamada et al (1998, Plant Physiology 118:591-598).*
Bowie et al, Science 247:1306-1310, 1990.*
McConnell et al, Nature 411 (6838):709-713, 2001.*
Gachotte et al (1996, The Plant Journal 9(3):391-398).*
Babiychuk et al., *Proc. Natl. Acad. Sci. USA*, 1997, 94:12722-12727.
Bowie et al., "Deciphering the Message in Protein Sequences: Tolerance to Amino Acid Substitutions," *Science*, 1990, 247:1306-1310.
Choe et al., "$_w$The *Arabidopsis dwf7/ste1* Mutant is Defective in the $\Delta^7$ Sterol C-5 Desaturation Step Leading to Brassinosteroid Biosynthesis," *The Plant Cell*, 1999, 11(2):207-221.
Finnegan and McElroy, "Transgene Inactivation:Plants Fights Back!," *Bio/technology*, 1994, 12:883-888.
Gachotte et al., "Isolation and Characterization of an *Arabidopsis thaliana* cDNA Encoding a $\Delta^7$ —Sterol-C-5 Desaturase by Functional Complementation of a Defective Yeast Mutant," *The Plant Journal*, 1996, 9(3):391-398.
Gachotte et al., "An *Arabidopsis* Mutant Deficient in Sterol Biosynthesis: Heterologous Complementation by ERG 3 encoding a $\Delta^7$ -Sterol-C-5-Desaturase from Yeast," *The Plant Journal*, 1995, 8(3):407-418.
Hamada et al., "Characterization of Transgenic Tobacco with an Increased x-Linolenic Acid Level 1," *Plant Physiology*, 1998, 118:591-598.
Husselstein et al., "$\Delta^7$ -Sterol-C5-desaturase: molecular characterization and functional expression of wild-type and mutant alleles," *Plant Molecular Biology*, 1999, 39:891-906.
GenBank Accession No. AAF32466 "Putative Sterol-C5 Desaturase (*Arabidopsis thaliana*)" dated Oct. 30, 2002.
GenBank Accession No. AB004539 "Shizosaccharomyces Pombe 28 kb Genomic DNA, Clone c1241" dated Sep. 11, 2002.
GenBank Accession No. AC021640 "*Arabidopsis thaliana* Chromosome III BAC F16B3 Genomic Sequence, Complete Sequence" dated Oct. 30, 2002.
GenBank Accession No. AF105034 "*Arabidopsis thaliana* $\Delta^7$ Sterol C-5 Desaturase (STE1) Gene Complete CDS" dated Jun. 10, 1999.
GenBank Accession No. L40390 "Candida Glabrata ERG3 Gene, Complete CDS" dated Jun 13, 1996.
GenBank Accession No. M62623 "*S. cerevisiae* C-5 Sterol Desaturase (erg3) Gene, Complete CDS" dated Apr. 27, 1993.
Haas et al., "Full-length messenger RNA sequences greatly improve genome annotation" *Genome Biology*, 2002, 3(6): 12 pages.

* cited by examiner

*Primary Examiner*—Stuart F. Baum
(74) *Attorney, Agent, or Firm*—Fish & Richardson P.C.

(57) ABSTRACT

Dwarf7 (dwf7) mutants and polypeptides, as well as methods of using the same, are disclosed. The dwf7 polynucleotides can be used in the production of transgenic plants which display at least one dwf7 phenotype, so that the resulting plants have altered structure or morphology.

5 Claims, 18 Drawing Sheets

FIG. 7

```
                        10        20        30        40
                GAAGATCGATCAATCAATCATCAAACTCTCTGTGTGCCAC 50         60         70         80         90        100
  41  ATGCATTACT ACTCTTGACT TGTTCAATAA ACGTAAACTA ACATCAATCC CGCCAATCTT 110        120        130        140        150        160
 101  CTTTCGTTTT CCCGCACCGA TCTCGGTCGA TCTCCGATTC ACATCGCCGC CGATAATCCT
                                                             M  A  A  D  N  A 170        180        190        200        210        220
 161  TATCTCATCC ACTTTCTTCA CCAAACCTCT TTTTACAACC GAATCGTTCT CACTCATCTT
       Y  L  M  Q  F  V  D  E  T  S  F  Y  N  R  I  V  L  S  H  L 230        240        250        260        270        280
 221  TTCCCCGCCA ATCTATGGA ACCCTTACCT CATTTTCTCC ACACATCCCT CCGAATTAC
       L  P  A  N  L  W  E  P  L  P  H  F  L  Q  T  H  L  R  N  Y 290        300        310        320        330        340
 281  CTCGCCCGAA CCCTACTATA CTTCATCTCC GGTTTCCTCT GCTGCTTCTA CATCTATTAC
       L  A  G  T  L  L  Y  F  I  S  G  F  L  W  C  F  Y  I  Y  Y
                                                  ▲

350        360        370        380        390        400
 341  CTTAAAATCA ACGTTTACCT TCCCAAAGCT CTCGACTTTC ACTTTTGTAT TCACTATTCC
       L  K  I  N  V  Y  L  P  K 410        420        430        440        450        460
 401  TTAATCGCTT TCTATGTTAT CGATTTTTCA ATTTAAGCAA GACGGTTTCT TCCTGTACTG 470        480        490        500        510        520
 461  TACACTAATT TGCATTTGAT CTGCATACTT CATCTTTGCA TTTATTCATT ATTTCTGCAT 530        540        550        560        570        580
 521  ATTCTCCATC TAACGGATTG AACACTTACT CGCTTATATA ACTTTTTCTG CAACCAATCA 590        600        610        620        630        640
 581  CAACTCGTAC ATCTTTGAAG TTCAATTTTC TACTTGCCAT TTAACTCCAC TTAAATTGTT
```

FIG. 8A

```
     650        660        670        680        690        700
641  TGTTCAACTC ATTGTCTACT TCAGACACA TCTTTTTCT GCTTCTCTGA GACTCTGTCT 710        720        730        740        750        760
701  TACTTTCAAA TCTTTTTTCC TCTGTTTTCC TTCAGATGCA ATTCCTACAA TAAAGCCTAT
                                            D  A  I  P  T  I  K  A  M 770        780        790        800        810        820
761  CCCTTTGCAA ATGTTTCTCC CAATGAAGCC TATGCCATCC TACACTCTTC TTCCAACTGT
      R  L  Q  M  F  V  A  M  K  A  M  P  H  Y  T  L  L  P  T  V 830        840        850        860        870        880
821  CTCCGACACT ATGATTGAAC CTGCTTGGAC CAAATGTTTT GCTAGCATAC ACGAATTCGG
      S  E  S  M  I  E  R  G  W  T  K  C  F  A  S  I  D  E  F  G 890        900        910        920        930        940
881  CTGGATTCTG TATTTTGTTT ACATCGCCAT CTATCTTGTT TTCGTTGACT TTGGTATTTA
      W  I  L  Y  F  V  Y  I  A  I  Y  L  V  F  V  E  F  G  I  Y 950        960        970        980        990       1000
941  TTGGATGCAC ACACAGCTTC ATGACATTAA GCCTCTCTAT AAGTATCTCC ATGCCACCCA
      W  M  H  R  E  L  H  D  I  K  P  L  Y  K  Y  L  H  A  T  H 1010       1020       1030       1040
1001 TCATATCTAC AACAAGCAGA ATACACTCTC TCCATTTCCC G
      H  I  Y  N  K  Q  N  T  L  S  P  F  R
```

FIG. 8B

```
                              1050       1060       1070       1080
                           CTAAGTCTT TTCACTTTCT TCTTCTTTAC TTCTTCTAAA 1090       1100       1110       1120       1130       1140
1081 AGATTCCTAC CATTTACTTT CTTACCACAA AAGACTTTCT CACCACCTCC TTCTACTCCA 1150       1160       1170       1180       1190       1200
1141 AATCACATTT TCCATTCCTT ATCCATAAAG TAACCACAAA CGCTACAATT ATATAAATCT 1210       1220       1230       1240       1250       1260
1201 CAGCTGCATT ACTTCACATA TGTCAGAGAC ACTTCTGACT TAACCAGACT TTACATCTTT 1270       1280       1290       1300       1310       1320
1261 CTGTTTCTCT TCTGCTCTCC CACTCATTGC AAATGACCAG AAGTTCTTTT ATCTACTTCC 1330       1340       1350       1360       1370       1380
1321 CTGCACTCTA TCTTCCTTAA TCCAAGCATC TGACATCTAA TATTACTTGT AACTTCCTTA 1390       1400       1410       1420       1430       1440
1381 CCTTTTTCTT TACAGGCCTT GCATTTCACC CAGTAGACGG GATACTTCAG GCTGTACCGC
                                     G  L  A  F  H  P  V  D  G  I  L  Q  A  V  P 1450       1460       1470       1480       1490       1500
1441 ATGTGATACC CCTCTTTATA GTGCCAATTC ATTTCACAAC TCATATAGGT CTTTTGTTCA
     H  V  I  P  L  F  I  V  P  I  H  F  T  T  H  I  G  L  L  F 1510       1520       1530       1540       1550       1560
1501 TCCAACCCAT ATGCACCCCG AACATCCATC ACTCCATCCA TGCCAACATC TGCCCACTAA
     M  E  A  I  W  T  A  H  I  H  D  C  I  H  G  N  I  W  P  V 1570       1580       1590       1600       1610       1620
1561 TGCCTGCAGC ATACCATACC ATACACCACA CCACATACAA GCATAACTAT GCTCATTATA
     M  G  A  G  Y  H  T  I  H  H  T  T  Y  K  H  N  Y  G  H  Y
```

FIG. 8C

```
       1630       1640       1650       1660       1670       1680
1621 CCATATCCAT CCATTCCATC TTTCCCTCTC TTACCCATCC TCTCTTACAA CAACATCACA
       T  I  H  H    D  H  H    F  C  S    L  R  D  P    L  L  E    E  D  D 1690       1700       1710       1720       1730       1740
1681 ACAAACACAC CTTCAACAAA CCACACTCAC AATCCCCACT TCCGTTTTGT TCTTCTGTTT
       H  K  D  S    F  K  K  A  E →

1750       1760       1770       1780       1790       1800
1741 TCTCTTCTGT TGTTCTTCTT CAAACTTTCA CCCTTTCTTC TTCTTTTTCT TCTTCTTCTT 1810       1820       1830       1840       1850       1860
1801 ATTCATGTGT CTCTCTCAAC CTTTCCAATT ATATTGTTAC AAACATTTGC TGTCTACTTT 1870       1880       1890
1861 AAAACATCTA AATCTTTCAT CATCTTTCCA
```

FIG. 8D

```
  1    MAADNAYLMQ FVDETSFYNR IVLSHLLPAN LWEPLPHFLQ TWLRNYLAGT
 51    LLYFISGFLW CFYIYYLKIN VYLPKDAIPT IKAMRLQMFV AMKAMPWYTL
101    LPTVSESMIE RGWTKCFASI DEFGWILYFV YIAIYLVFVE FGIYWMHREL
151    HDIKPLYKYL HATHHIYNKQ NTLSPFAGLA FHPVDGILQA VPHVIALFIV
201    PIHFTTHIGL LFMEAIWTAN IHDCIHGNIW PVMGAGYHTI HHTTYKHNYG
251    HYTIWMDWMF GSLRDPLLEE DDNKDSFKKA E
```

FIG. 9

```
         10                      30                      50
          .                       .                       .
GTTTGGTATTTATTGGATGCACAGAGAGCTTCATGACATTAAGCCTCTCTATAAGTATCT
CAAACCATAAATAACCTACGTGTCTCTCGAAGTACTGTAATTCGGAGAGATATTCATAGA 70                      90                     110
          .                       .                       .
CCATGCCACCCATCATATCTACAACAAGCAGAATACACTCTCTCCATTTGCCGGTAAGTG
GGTACGGTGGGTAGTATAGATGTTGTTCGTCTTATGTGAGAGAGGTAAACGGCCATTCAC 130                     150                     170
          .                       .                       .
TTTTCAGTTTGTTCTTCTTTAGTTCTTGTAAAAGATTGGTAGCATTTAGTTTCTTACCAG
AAAAGTCAAACAAGAAGAAATCAAGAACATTTTCTAACCATCGTAAATCAAAGAATGGTC 190                     210                     230
          .                       .                       .
AAAAGACTTTGTCAGCAGCTGCTTGTACTCCAAATCACATTTTGCATTCCTTATCCATAA
TTTTCTGAAACAGTCGTCGACGAACATGAGGTTTAGTGTAAAACGTAAGGAATAGGTATT 250                     270                     290
          .                       .                       .
AGTAACCAGAAAGGCTAGAATTATATAAATGTCAGCTGCATTACTTCACATATGTCAGAG
TCATTGGTCTTTCCGATCTTAATATATTTACAGTCGACGTAATGAAGTGTATACAGTCTC 310                     330                     350
          .                       .                       .
AGACTTCTGACTTAACCAGAGTTTAGATCTTTGTGTTTCTCTTCTGGTCTCGGACTGATT
TCTGAAGACTGAATTGGTCTCAAATCTAGAAACACAAAGAGAAGACCAGAGCCTGACTAA 370                     390                     410
          .                       .                       .
GGAAATGACGAGAAGTTCTTTTATCTACTTCCCTGGAGTGTATCTTGGTTAATCCAAGGA
CCTTTACTGCTCTTCAAGAAAATAGATGAAGGGACCTCACATAGAACCAATTAGGTTCCT 430                     450                     470
          .                       .                       .
TGTGACATCTAAATATTACTTGTAACTTCCTTACGTTTTTGTTTACAGGGCTTGCATTCA
ACACTGTAGATTTATAATGAACATTGAAGGAATGCAAAAACAAATGTCCCGAACGTAAGT 490                     510                     530
          .                       .                       .
CCCAGTAGACGGGATACTTAAGGCTGTACCGCATGTGATAGCGCTGTTATAGTGCCAATT
GGGTCATCTGCCCTATGAATTCCGACATGGCGTACACTATCGCGACAATATCACGGTTAA 550                     570                     590
          .                       .                       .
CATTTCACAACTCATATAGGTCTTTTGTTCATGGAAGCGATATGGACGGCGAACATCCAT
GTAAAGTGTTGAGTATATCCAGAAAACAAGTACCTTCGCTATACCTGCCGCTTGTAGGTA
```

FIG. 10A

```
                610                    630                    650
                 .                      .                      .
GACTGCATCCATGGCAACATCTGGCCAGTAATGGGTGCAGGATACCATACGATACACCAC
CTGACGTAGGTACCGTTGTAGACCGGTCATTACCCACGTCCTATGGTATGCTATGTGGTG 670                    690                    710
                 .                      .                      .
ACGACATACAAGCATAACTATGGTCATTATACCATATGGATGGATTGGATGTTTGGCTCT
TGCTGTATGTTCGTATTGATACCAGTAATATGGTATACCTACCTAACCTACAAACCGAGA 730                    750                    770
                 .                      .                      .
CTTAGGGATCCTCTCTTAGAAGAAGATGACAACAAAGACAGCTTCAAGAAAGCAGAGTGA
GAATCCCTAGGAGAGAATCTTCTTCTACTGTTGTTTCTGTCGAAGTTCTTTCGTCTCACT 790                    810                    830
                 .                      .                      .
GAATGCCCACTTGGGTTTTGTTCTTCTGTTTTGTCTTGTGTTGTTGTTGTTCAAAGTTTC
CTTACGGGTGAACCCAAAACAAGAAGACAAAACAGAACACAACAACAACAAGTTTCAAAG 850                    870                    890
                 .                      .                      .
AGCCTTTCTTGTTCTTTTTCTTCTTCTTCTTATTCATGTGTCTCTCTCAACCTTTCCAAT
TCGGAAAGAACAAGAAAAAGAAGAAGAAGAATAAGTACACAGAGAGAGTTGGAAAGGTTA 910                    930                    950
                 .                      .                      .
TATATTGTTACAAACATTTGCTGTCTAGTTTAAAACATGTAAATGTTTGATGATCTTTGC
ATATAACAATGTTTGTAAACGACAGATCAAATTTTGTACATTTACAAACTACTAGAAACG 970                    990                    1010
                 .                      .                      .
AAGACTCCATTTTTGTTTAAGGTAAACCTTGAATCTCATAGATTGTCGATTGTTGGTATT
TTCTGAGGTAAAAACAAATTCCATTTGGAACTTAGAGTATCTAACAGCTAACAACCATAA 1030                   1050                   1070
                 .                      .                      .
TCCATTTTCAGGTACGGTTCTGTAGACTGTAGTCTTGCTGACCAGTCCGGCTTAACCACC
AGGTAAAAGTCCATGCCAAGACATCTGACATCAGAACGACTGGTCAGGCCGAATTGGTGG 1090                   1110                   1130
                 .                      .                      .
CCAAATTTCAAAGATCTCAcCAATCAAAATGCTGGCTGGCCCCAATATATAGATGGGCCA
GGTTTAAAGTTTCTAGAGTgGTTAGTTTTACGACCGACCGGGGTTATATATCTACCCGGT 1150                   1170                   1190
                 .                      .                      .
GTTAATCCGTCTAGCTTTACTCTTTAGACCTACCTTAGACAGTTAGACACCTGCTAATTA
CAATTAGGCAGATCGAAATGAGAAATCTGGATGGAATCTGTCAATCTGTGGACGATTAAT
```

FIG. 10B

```
         1210                    1230                    1250
          .                       .                       .
ATGAGTTTCCTTTTTCTTGTTCAGCAAGTTACCTGTGTTACTTGAGAGTTGAGTTAATGG
TACTCAAAGGAAAAAGAACAAGTCGTTCAATGGACACAATGAACTCTCAACTCAATTACC 1270                    1290                    1310
          .                       .                       .
TAGTAAACGCAATTTAACCCTTATAAGTTTAATCGTATTCAACGAATGACCCAGAGACTT
ATCATTTGCGTTAAATTGGGAATATTCAAATTAGCATAAGTTGCTTACTGGGTCTCTGAA 1330                    1350                    1370
          .                       .                       .
TAAATAAATCCATCGTAACCCTCCACTTCAAAATTCTTTTTAAAAAGTAGCAAATCATTT
ATTTATTTAGGTAGCATTGGGAGGTGAAGTTTTAAGAAAAATTTTTCATCGTTTAGTAAA 1390                    1410                    1430
          .                       .                       .
AAATATTGTAAGTTTGCTTCATTCGAAATTGTAGCTACAGATCTCAAAGCTCCTCCTGTT
TTTATAACATTCAAACGAAGTAAGCTTTAACATCGATGTCTAGAGTTTCGAGGAGGACAA 1450                    1470                    1490
          .                       .                       .
GGCCATATCTCTCTCTAACAAACGCATAGTAACACTTGACCACAGTTTGACTTCTCGGCG
CCGGTATAGAGAGAGATTGTTTGCGTATCATTGTGAACTGGTGTCAAACTGAAGAGCCGC 1510                    1530                    1550
          .                       .                       .
GTTTCATGGCGGCGACTATGGCAGATTATAATGATCAGATCGTCAATGAGACCTCTTTTT
CAAAGTACCGCCGCTGATACCGTCTAATATTACTAGTCTAGCAGTTACTCTGGAGAAAAA
      M   A   A   T   M   A   D   Y   N   D   Q   I   V   N   E   T   S   F   Y 1570                    1590                    1610
          .                       .                       .
ACAACCGAAtGGTTCTGAGTCACCTTTTGCCGgTGAATCTATGGGAACCTTTACCaCATT
TGTTGGCTTaCCAAGACTCAGTGGAAAACGGCcACTTAGATACCCTTGGAAATGGtGTAA
  N   R   M   V   L   S   H   L   L   P   V   N   L   W   E   P   L   P   H   F 1630                    1650                    1670
          .                       .                       .
TCCTCCAGACATGGCTCCGGAACTACCTCGCCGGAAACATACTCTACTTCATCTCCGGCT
AGGAGGTCTGTACCGAGGCCTTGATGGAGCGGCCTTTGTATGAGATGAAGTAGAGGCCGA
  L   Q   T   W   L   R   N   Y   L   A   G   N   I   L   Y   F   I   S   G   F 1690                    1710                    1730
          .                       .                       .
TCCTCTGGTGCTTCTACATCTATTACCTTAAACTCAACGTTTACGTCCCCAAAGGTTACT
AGGAGACCACGAAGATGTAGATAATGGAATTTGAGTTGCAAATGCAGGGGTTTCCAATGA
  L   W   C   F   Y   I   Y   Y   L   K   L   N   V   Y   V   P   K
```

FIG. 10C

```
         1750                    1770                   1790
           .                       .                      .
TTTTTCAATTTCGATGTTCTGTTTTGAAACCTTTCTTTTGTTGATTCCTTCGATTGTATC
AAAAAGTTAAAGCTACAAGACAAAACTTTGGAAAGAAAACAACTAAGGAAGCTAACATAG 1810                    1830                   1850
           .                       .                      .
GCCTGATAGATTGTGTTATACGTTAACCTTTTTTTCTTACTGTTACTTTCAGTTCTTGTC
CGGACTATCTAACACAATATGCAATTGGAAAAAAGAATGACAATGAAAGTCAAGAACAG 1870                    1890                   1910
           .                       .                      .
TTCTACTTCTCATTTAATTAGTTTTAAAGTTTAATATTTTTGGCTAATCCACATTTTTTA
AAGATGAAGAGTAAATTAATCAAAATTTCAAATTATAAAAACCGATTAGGTGTAAAAAAT 1930                    1950                   1970
           .                       .                      .
AGTTGAATCTTCCATGAAATTTGAGCTCAAAATATACCATGAAATTGAAATTTGTGGTTC
TCAACTTAGAAGGTACTTTAAACTCGAGTTTTATATGGTACTTTAACTTTAAACACCAAG 1990                    2010                   2030
           .                       .                      .
TTAGTTCTATTTCTTGCTTGGTTTCTTCTATTTTTGTGGTTAGAATCCATTCCTACGAGA
AATCAAGATAAAGAACGAACCAAAGAAGATAAAAACACCAATCTTAGGTAAGGATGCTCT
                                                   E  S  I  P  T  R 2050                    2070                   2090
           .                       .                      .
AAGGCAATGCTTTTGCAAATATACGTGGCAATGAAGGCTATGCCTTGGTACACTCTTCTT
TTCCGTTACGAAAACGTTTATATGCACCGTTACTTCCGATACGGAACCATGTGAGAAGAA
 K  A  M  L  L  Q  I  Y  V  A  M  K  A  M  P  W  Y  T  L  L 2110                    2130                   2150
           .                       .                      .
CCAGCTGTCTCTGAGTATATGATCGAGCATGGTTGGACCAAATGTTACTCTACACTTGAC
GGTCGACAGAGACTCATATACTAGCTCGTACCAACCTGGTTTACAATGAGATGTGAACTG
 P  A  V  S  E  Y  M  I  E  H  G  W  T  K  C  Y  S  T  L  D 2170                    2190                   2210
           .                       .                      .
CATTTCAACTGGTTCCTCTGTTTCCTCTACATAGCTCTCTATCTTGTTTTAGTTGAGTTt
GTAAAGTTGACCAAGGAGACAAAGGAGATGTATCGAGAGATAGAACAAAATCAACTCAAa
 H  F  N  W  F  L  C  F  L  Y  I  A  L  Y  L  V  L  V  E  F 2230                    2250                   2270
           .                       .                      .
ATGATTTATTGGGTTCACAAAGAGCTTCATGACATTAAATTTCTCTATAAGCATCTCCAT
TACTAAATAACCCAAGTGTTTCTCGAAGTACTGTAATTTAAAGAGATATTCGTAGAGGTA
 M  I  Y  W  V  H  K  E  L  H  D  I  K  F  L  Y  K  H  L  H
```

FIG. 10D

```
         2290                    2310                     2330
          .                       .                        .
GCTACCCATCATATGTACAACAAGCAAAACACACTCTCTCCATTTGCCGGTATGTCAAAG
CGATGGGTAGTATACATGTTGTTCGTTTTGTGTGAGAGAGGTAAACGGCCATACAGTTTC
 A   T   H   H   M   Y   N   K   Q   N   T   L   S   P   F   A 2350                    2370                     2390
          .                       .                        .
CTATATGTTCTCAATCTAAATTCAAGAGCTTGTATCAATGGTGACTTCTTTACTTGATGT
GATATACAAGAGTTAGATTTAAGTTCTCGAACATAGTTACCACTGAAGAAATGAACTACA 2410                    2430                     2450
          .                       .                        .
TTTTCGGGTTTTCAGGGCTCGCATTCCATCCGCTGGACGGGATACTTCAGGCTATACCGC
AAAAGCCCAAAAGTCCCGAGCGTAAGGTAGGCGACCTGCCCTATGAAGTCCGATATGGCG
           G   L   A   F   H   P   L   D   G   I   L   Q   A   I   P   H 2470                    2490                     2510
          .                       .                        .
ACGTGATAGCGCTGTTTATAGTGCCGATTCATCTCATAACACATCTGAGTCTTTTGTTTT
TGCACTATCGCGACAAATATCACGGCTAAGTAGAGTATTGTGTAGACTCAGAAAACAAAA
  V   I   A   L   F   I   V   P   I   H   L   I   T   H   L   S   L   L   F   L 2530                    2550                     2570
          .                       .                        .
TGGAAGGGATATGGACAGCAAGCATCCATGATTGCATACATGGtAACATCTGGCCTATAA
ACCTTCCCTATACCTGTCGTTCGTAGGTACTAACGTATGTACCaTTGTAGACCGGATATT
  E   G   I   W   T   A   S   I   H   D   C   I   H   G   N   I   W   P   I   M 2590                    2610                     2630
          .                       .                        .
TGGGTGCAGGATACCATACCATACACCATACAACATACAAGCATAACTATGGTCATTATa
ACCCACGTCCTATGGTATGGTATGTGGTATGTTGTATGTTCGTATTGATACCAGTAATAt
  G   A   G   Y   H   T   I   H   H   T   T   Y   K   H   N   Y   G   H   Y   T 2650                    2670                     2690
          .                       .                        .
CCATATGGATGGaCTGGATGTTTGGCTCTCTTATGGTTCCTTTAGCAGAAAAAGACAGTT
GGTATACCTACCtGACCTACAAACCGAGAGAATACCAAGGAAATCGTCTTTTTCTGTCAA
  I   W   M   D   W   M   F   G   S   L   M   V   P   L   A   E   K   D   S   F 2710                    2730                     2750
          .                       .                        .
TCAAGGAGAAAGAAAAGTGAGAATGTTCAATGCTCACATGTATTCTTCATATGTTGCTCT
AGTTCCTCTTTCTTTTCACTCTTACAAGTTACGAGTGTACATAAGAAGTATACAACGAGA
    K   E   K   E   K   *

2770                    2790                     2810
          .                       .                        .
TCTCGTGACTCTTATTAAAACCTTTCTAATCACTTTGGTGGAATTAAAAACATGACTGCA
AGAGCACTGAGAATAATTTTGGAAAGATTAGTGAAACCACCTTAATTTTTGTACTGACGT
```

*FIG. 10E*

```
              2830                    2850                      2870
TAATTTGATGCAAAGTTTCAGACTTTTATTGCTAAAAATCTCTGATGATTATTAACCTCA
ATTAAACTACGTTTCAAAGTCTGAAAATAACGATTTTTAGAGACTACTAATAATTGGAGT 2890                    2910
ATTATATAATTGcTGGATGAAGAGTTCAAATTTGGACTAAATCTG
TAATATATTAACgACCTACTTCTCAAGTTTAAACCTGATTTAGAC
```

*FIG. 10F*

```
  1  maatmadynd qivnetsfyn rmvlshllpv nlweplphfl qtwlrnylag
 51  nilyfisgfl wcfyiyylkl nvyvpkesip trkamllqiy vamkampwyt
101  llpavseymi ehgwtkcyst ldhfnwflcf lyialylvlv efmiywvhke
151  lhdikflykh lhathhmynk qntlspfagl afhpldgilq aiphvialfi
201  vpihlithls llflegiwta sihdcihgni wpimgagyht ihhttykhny
251  ghytiwmdwm fgslmvplae kdsfkekek
```

FIG. 11

DWF7 MUTANTS

CROSS-REFERENCE TO RELATED APPLICATION

This application is a divisional of U.S. application Ser. No. 09/775,879, filed Feb. 2, 2001, now abandoned, which claims priority to provisional patent application Ser. No. 60/179,901, filed Feb. 2, 2000, both of which are incorporated herein by reference in their entireties.

TECHNICAL FIELD

The present invention relates generally to plants that display altered structure or morphology and to the genes imparting such pheontypes. In particular, the present invention pertains to Dwarf7 (dwf7) mutants and methods of using the same.

BACKGROUND OF THE INVENTION

Sterols are known to play at least two critical roles in plants: as bulk components of membranes regulating stability and permeability (Bach et al. (1997) Prog. Lipid Res. 36:197–226) and as precursors of growth-promoting brassinosteroids (BRs; Fujioka and Sakurai (1997) Nat. Prod. Rep. 14:1–10). Lesions in brassinosteroid (BR) biosynthetic genes result in characteristic dwarf phenotypes in plants. Understanding the regulation of BR biosynthesis demands continued isolation and characterization of mutants corresponding to the genes involved in BR biosynthesis.

Sterol biosynthesis in plants has been studied extensively through enzyme purification or gene cloning (Grunwald (1975) Annu. Rev. Plant Physiol. 26:209–236; Goodwin (1979) Annu. Rev. Plant Physiol. 30:369–404; Benveniste (1986) Annu. Rev. Plant Physiol. 37:275–308; Bach and Benveniste (1997) Prog. Lipid Res. 36:197–226). FIG. 1 shows the proposed biosynthetic pathway from squalene to brassinolide (BL). A major difference between photosynthetic and nonphotosynthetic organisms is that cyclization of squalene 2,3-oxide is bifurcated to a different route for each system (Benveniste (1986) Annu. Rev. Plant Physiol. 37:275–308). In animals and yeast, squalene 2,3-oxide is cyclized to lanosterol, whereas in photosynthetic organisms it is cyclized to cycloartenol (Nes and McKean (1977) Biochemistry of Steroids and Other Isopentenoids. (Baltimore, Md.: University Park Press)). Accordingly, photosynthetic organisms require somewhat different biosynthetic enzymes, such as cycloartenol synthase (Corey et al. (1993) Proc. Natl. Acad. Sci. USA 90:11628–11632) and cycloeucalenol-obtusifoliol isomerase, which are required to open the cyclopropane ring in cycloartenol (FIG. 1). However, most of the enzymatic steps are shared between the two different pathways.

In plants, sterols are subject to a series of modifications before conversion to BL. Different sterols, such as 24-methylenecholesterol (24-MC), campesterol (CR), isofucosterol, and sitosterol, are converted to the BL congeners dolicholide, BL, 28-homodolicholide, and 28-homoBL, respectively, in a species-specific manner (Fujioka et al. (1997) Plant Cell 9:1951–1962; Sasse (1997) Physiol. Plant. 100:696–701). The BR-specific pathway diverges into the early and the late C-6 oxidation pathways. In the early C-6 oxidation pathway, introduction of a 6-oxo group occurs before the vicinal hydroxylation reactions at the side chain, whereas it occurs after these hydroxylations in the late C-6 oxidation pathway (FIG. 1; Choi et al. (1997) Phytochemistry 44:609–613).

Several mutants, such as constitutive photomorphogenesis and dwarfism (cpd), deetiolated2 (det2), and dwarf4 (dwf4), have been shown to be defective in the BR-specific pathway (Li et al. (1996) Science 272:398–401; Li et al. (1997) Proc. Natl. Acad. Sci. USA 94:3554–3559; Szekeres et al. (1996) Cell 85:171–182; Choe et al. (1998) Plant Cell 10:231–243). These BR biosynthetic dwarfs share a characteristic dwarf phenotype, which includes short robust stems, reduced fertility, prolonged life cycle, and dark-green, round, and curled leaves when grown in the light. In the dark, these mutants exhibit short hypocotyls and expanded cotyledons. cpd (dwf3) mutants are only rescued by 23α-hydroxylated compounds (Szekeres et al. (1996) Cell 85:171–182). The CPD gene was shown to encode a cytochrome P450 steroid hydroxylating enzyme (CYP90A1). In addition, Li et al. (1996) Science 272: 398–401 and Li et al. (1997) Proc. Natl. Acad. Sci. USA 94:3554–3559 showed that det2/dwf6 is blocked in the C-5 reduction step. DET2 was found to be homologous to steroid 5α-reductases. Like its animal equivalents, DET2 successfully converted progesterone (3-oxo-$\Delta^{4,5}$ steroid) to 4,5-dihydroprogesterone in a human cell line. In addition, the human 5α-reductase gene effectively complemented det2 mutants (Li et al. (1997) Proc. Natl. Acad. Sci. USA 94:3554–3559). Recently, it has been shown that DWF4 encodes a cytochrome P450 whose amino acid sequence is 43% identical to CPD; DWF4 has been named CYP90B1 (Choe et al. (1998) Plant Cell 10:231–243). Based on results from feeding studies using BR biosynthetic intermediates, the proposed rate-limiting step of BR biosynthesis, 22α-hydroxylation, is now known to be blocked in dwf4 mutants.

In the plant sterol biosynthetic pathway, several of the genes have been cloned or identified based on heterologous expression or sequence similarity. First, Corey et al. (1993) *Proc. Natl. Acad. Sci. USA* 90:11628–11632 isolated a cycloartenol synthase cDNA by heterologous complementation of yeast mutants lacking lanosterol synthase. In addition, two types of cDNAs encoding sterol methyltransferases have been isolated from soybean (Shi et al. (1996) J. Biol. Chem. 271:9384–9389) and Arabidopsis (Husselstein et al. (1996) FEBS Lett. 381:87–92). The Arabidopsis cDNA has been shown to mediate a second methyltransferase step leading to $C_{29}$ sterols (Bouvier-Nave et al. (1997) Eur. J. Biochem. 246:518–529). For the 14α-demethylation reaction, Bak et al. (1997) Plant J. 11:191–201 cloned the cDNA encoding the 14-αdemethylase cytochrome P450 enzyme (CYP51) from *Sorghum bicolor*. Based on sequence similarity, Grebenok et al. (1997) Plant Mol. Biol. 34:891–896 identified an Arabidopsis sterol C-8 isomerase (GenBank accession number AF030357). Furthermore, an ERGOSTEROL25 (ERG25) homolog for Arabidopsis (C-4 demethylase) also has been discovered in the genome sequencing project (GenBank accession number AL021635). Finally, a sterol C-7 reductase has been cloned by heterologous expression of an Arabidopsis cDNA in yeast (Lecain et al. (1996) J. Biol. Chem. 271:10866–10873).

As compared with the wealth of cloned genes in sterol biosynthesis, only one mutant has been found in these genes. Gachotte et al. (1995) Plant J. 8:407–416 screened an ethyl methanesulfonate (EMS)-induced mutant population (22,000 $M_2$ plants) for mutants displaying an altered sterol profile. The screen yielded one mutant, sterol1 (ste1), whose endogenous level of C-5-desaturated sterols is reduced to 30% of that of the wild type. Expression of the yeast gene ERG3 (the gene for $\Delta^7$ sterol C-5 desaturase) in the ste1-1 mutant increased the level of C-5-desaturated sterols 1.7- to 2.8-fold compared with the ste1-1 control, suggesting functional conservation of the enzymes from yeast and plants. However, visible phenotypes were not found in ste1-1 plants. Thus, the authors hypothesized that the residual 30% level of C-5-desaturated sterols was sufficient for the growth of plants.

A large collection of BR dwarf mutants have been characterized. Of the eight dwf loci identified to date, dwf3 (cpd; Szekeres et al. (1996) Cell 85:171–182), dwf4 (Choe et al. (1998) Plant Cell 10:231–243), and dwf6 (det2; Li et al. (1996) Science 272:398–401) have been shown to act in the BR biosynthetic pathway, whereas dwf2 (bri1) probably is involved in BR perception (Clouse et al. (1996) Plant Physiol. 111:671–678; Li and Chory (1997) Cell 90:929–938).

DISCLOSURE OF THE INVENTION

The present invention is based on the discovery of various mutants of a BR biosynthetic locus, designated dwarf7 (dwf7). The STE1 locus in dwf7 mutants contain loss-of-function mutations. Two allelic variants of dwf7 have been characterized, dwf7-1 and dwf7-2, also designated ste1-2 and ste1-3, respectively. A homologue of the dwf7 mutants, HDF7, is also described herein. Feeding studies with BR biosynthetic intermediates and analysis of endogenous levels of BR and sterol biosynthetic intermediates indicate that the defective step in the dwf7 mutants resides before the production of 24-methylenecholesterol in the sterol biosynthetic pathway. Furthermore, results from feeding studies with $^{13}$C-labeled mevalonic acid and compactin show that the defective step is specifically the $\Delta^7$ sterol C-5 desaturation. Sequencing of the STE1 locus in the two dwf7 variants shows premature stop codons in the first (dwf7-2) and the third (dwf7-1) exons. Thus, the reduction of BRs in dwf7 is due to a shortage of substrate sterols and is the direct cause of the dwarf phenotype in dwf7.

Accordingly, in one embodiment, the present invention is directed to an isolated dwf7 polynucleotide that imparts at least one dwf7 mutant phenotype when expressed in a plant. The polynucleotide is selected from the group consisting of (a) a polynucleotide comprising the nucleotide sequence depicted at positions 143 to 322, inclusive, of FIGS. 8A–8D; (b) a polynucleotide comprising the nucleotide sequence depicted at positions 143 to 1552, inclusive, of FIGS. 8A–8D; (c) a polynucleotide comprising a nucleotide sequence having at least about 70% identity to the nucleotide sequence of (a) or (b); (d) a fragment of (a), (b) or (c) comprising at least about 15 contiguous nucleotides; and (e) complements of (a), (b), (c), (d) or (e).

In other embodiments, the present invention is directed to an isolated dwf7 polynucleotide that imparts at least one dwf7 mutant phenotype when expressed in a plant. The polynucleotide is selected from the group consisting of (a) a polynucleotide comprising the nucleotide sequence depicted at positions 1506 to 2720, inclusive, of FIGS. 10A–10F; (b) a polynucleotide comprising a nucleotide sequence having at least 70% identity to the nucleotide sequence of (b); (c) a fragment of (a) or (b) comprising at least 15 contiguous nucleotides; and (d) complements of (a), (b), (c) or (d).

In additional embodiments, the present invention is directed to recombinant vectors comprising the isolated dwf7 polynucleotides described above, and control elements that are operably linked to the polynucleotides whereby a coding sequence within the polynucleotides can be transcribed and translated in a host cell, and at least one of the control elements is heterologous to the coding sequence. Also provided are host cells transformed with the recombinant vectors, and methods of producing a DWF7 polypeptide comprising providing a population of host cells as described above and culturing the population of cells under conditions whereby the DWF7 polypeptide encoded by the coding sequence present in the recombinant vector is expressed.

In yet further embodiments, the subject invention is directed to a transgenic plant comprising a polynucleotide described above, as well as methods of producing a transgenic plant comprising the steps of introducing a polynucleotide into a plant cell to produce a transformed plant cell; and producing a transgenic plant from the transformed plant cell.

In an additional embodiment, the invention is directed to a method for altering the sterol composition of a plant relative to the wild-type plant comprising introducing a polynucleotide as described above into a plant cell to produce a transformed plant cell and producing a transgenic plant from the transformed plant cell, wherein the transgenic plant has an altered sterol composition relative to the wild-type plant, such as an altered cholesterol composition relative to the wild-type plant.

In still further embodiments, the invention is directed to isolated DWF7 polypeptides encoded by the polynucleotides as described above. In certain embodiments, the polypeptide consists of the amino acid sequence depicted at positions 1–60, inclusive, of FIG. 9 or the amino acid sequence depicted at positions 1–230, inclusive, of FIG. 9. In other embodiments, the polypeptide consists of the amino acid sequence depicted at positions 1–279, inclusive, of FIG. 11.

In other embodiments, the subject invention is directed to an isolated control element having at least about 70% identity to a control element found within nucleotide positions 43–142 of FIGS. 8A–8D, or 1–1505 of FIGS. 10A–10F, a recombinant vector comprising the control element and a polynucleotide comprising a coding sequence which is heterologous to the control element, host cells transformed with the recombinant vector, and methods of producing a recombinant polypeptide comprising providing a population of the host cells and culturing the population of cells under conditions whereby the recombinant polypeptide encoded by the coding sequence present in the recombinant vector is expressed.

These and other embodiments of the present invention will readily occur to those of ordinary skill in the art in view of the disclosure herein.

BRIEF DESCRIPTION OF THE FIGURES

FIG. 7 depicts a multiple sequence alignment of DWF7/STE1 with known sequences for $\Delta^7$ sterol C-5 desaturases. The GenBank accession numbers for the sequences are M62623 (S. cerevisiae)(SEQ ID NO:16), AB004539 (Schizosaccharomyces pombe)(SEQ ID NO:17), L40390 (C.glabrata)(SEQ ID NO:15), and AF105034 (DWF7/STE, Arabidopsis)(SEQ ID NO:18). The conserved transmembrane domains and histidine clusters are boxed and labeled. The positions of the premature stop codons in dwf7-1 and dwf7-2 are indicated with filled circles. Histidine residues in each conserved histidine box are identified with filled triangles. A consensus sequence (SEQ ID NO:19) is shown in the bottom row of the alignment. Capital letters stand for residues conserved among all sequences, whereas lowercase letters mean ≧50% identical. Dashes indicate gaps introduced to maximize alignment. Multiple sequence alignment was performed using PILEUP in the Genetics Computer Group software (Madison, Wis.) with a gap creation penalty of 4 and gap extension parameter of 1. The annotation of the aligned sequences was performed using the ALSCRIIPT software (Barton (1993) Protein Eng. 6:37–40).

FIGS. 8A–8D (SEQ ID NO:20) depict the complete gene sequence of dwf7, denoted by a dark grey bar. The premature stop codons for dwf7- 1 and dwf7-2 are shown with triangles at nucleotide positions 1552 and 322, respectively. The coding sequence and corresponding amino acid sequence are represented by a light grey bar. The mRNA sequence is represented by a black bar and is shown in three segments. The gene includes two introns (positions 369–735 and 1042–1395) and three exons.

FIG. 9 (SEQ ID NO:21) shows the amino acid sequence corresponding to the coding sequence designated in FIGS. 8A–8D. The polypeptide sequences corresponding to the dwf7-2 and dwf7-1 alleles occur at positions 1–60 (SEQ ID NO:24) and 1–230 (SEQ ID NO:25), respectively.

FIGS. 10A–10F (SEQ ID NO:22) show the gene sequence of the dwf7 homologue, HDF7. The coding sequence and corresponding amino acid sequence are shown in three segments (exons), occuring at positions 1506–1734, 2024–2329 and 2416–2720 of the figures. The 5' UTR is shown at positions 1–1505 and the 3' UTR occurs at positions 2721–2925.

FIG. 11 (SEQ ID NO:23) shows the amino acid sequence corresponding to the coding sequence designated in FIGS. 10A–10F. The polypeptide sequence corresponding to the HDF7 dwf7 polypeptide occurs at positions 1–230 of the figure.

DETAILED DESCRIPTION OF THE INVENTION

Figure 1:
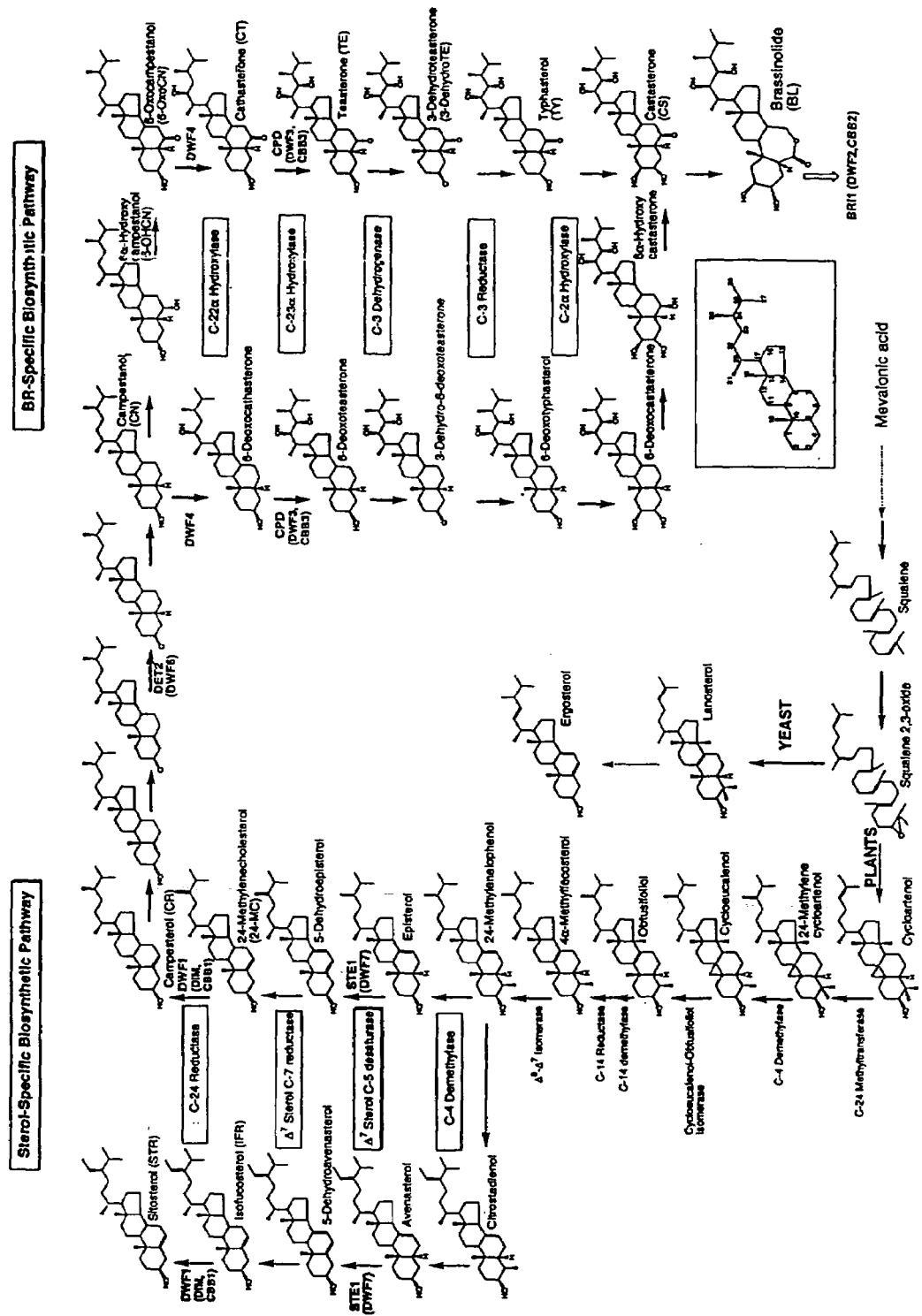
FIG. 1 shows the proposed BL biosynthetic pathway from squalene to BL. The BL biosynthetic pathway is divided into the sterol-specific pathway, squalene to campesterol, and the BR-specific pathway, campesterol to brassinolide. Common names for the compounds are labeled, and proposed enzymes involved in each reaction are boxed and labeled. Genes identified by mutants are marked. The acronyms for some compounds are in parentheses. In the inset, the carbon atoms of the sterol core rings and side chain are numbered.

The practice of the present invention will employ, unless otherwise indicated, conventional methods of protein chemistry, biochemistry, recombinant DNA techniques and pharmacology, within the skill of the art. Such techniques are explained fully in the literature. See, e.g., Evans, et al., *Handbook of Plant Cell Culture* (1983, Macmillan Publishing Co.); Binding, *Regeneration of Plants, Plant Protoplasts* (1985, CRC Press); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990).

All publications, patents and patent applications cited herein, whether supra or infra, are hereby incorporated by reference in their entirety.

It must be noted that, as used in this specification and the appended claims, the singular forms "a", "an" and "the" include plural referents unless the content clearly dictates otherwise. Thus, for example, reference to "a polypeptide" includes a mixture of two or more polypeptides, and the like.

The following amino acid abbreviations are used throughout the text:

| | |
|---|---|
| Alanine: Ala (A) | Arginine: Arg (R) |
| Asparagine: Asn (N) | Aspartic acid: Asp (D) |
| Cysteine: Cys (C) | Glutamine: Gln (Q) |
| Glutamic acid: Glu (E) | Glycine: Gly (G) |
| Histidine: His (H) | Isoleucine: Ile (I) |
| Leucine: Leu (L) | Lysine: Lys (K) |
| Methionine: Met (M) | Phenylalanine: Phe (F) |
| Proline: Pro (P) | Serine: Ser (S) |
| Threonine: Thr (T) | Tryptophan: Trp (W) |
| Tyrosine: Tyr (Y) | Valine: Val (V) |

I. Definitions

In describing the present invention, the following terms will be employed, and are intended to be defined as indicated below.

The terms "nucleic acid molecule" and "polynucleotide" are used interchangeably and refer to a polymeric form of nucleotides of any length, either deoxyribonucleotides or ribonucleotides, or analogs thereof. This term refers only to the primary structure of the molecule and thus includes double- and single-stranded DNA and RNA. It also includes known types of modifications, for example, labels which are known in the art, methylation, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example proteins (including e.g., nucleases, toxins, antibodies, signal peptides, poly-L-lysine, etc.), those with intercalators (e.g., acridine, psoralen, etc.), those containing chelates (e.g., metals, radioactive metals, boron, oxidative metals, etc.), those containing alkylators, those with modified linkages (e.g., alpha anomeric nucleic acids, etc.), as well as unmodified forms of the polynucleotide. Polynucleotides may have any three-dimensional structure, and may perform any function, known or unknown. Nonlimiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term polynucleotide sequence is the alphabetical representation of a polynucleotide molecule. This alphabetical representation can be input into databases in a computer having a central processing unit and used for bioinformatics applications such as functional genomics and homology searching.

Techniques for determining nucleic acid and amino acid "sequence identity" are known in the art. Typically, such techniques include determining the nucleotide sequence of the mRNA for a gene and/or determining the amino acid sequence encoded thereby, and comparing these sequences to a second nucleotide or amino acid sequence. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, *Advances in Applied Mathematics* 2:482–489 (1981). This algorithm can be applied to amino acid sequences by using the scoring matrix developed by Dayhoff, *Atlas of Protein Sequences and Structure*, M. O. Dayhoff ed., 5 suppl. 3:353–358, National Biomedical Research Foundation, Washington, D.C., USA, and normalized by Gribskov, *Nucl. Acids Res.* 14(6):6745–6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+ PDB+GenBank CDS translations+Swiss protein+Spupdate+ PIR. Details of these programs can be found at the following internet address: http://www.ncbi.nlm.nih.gov/cgi-bin/BLAST.

Alternatively, the degree of sequence similarity between polynucleotides can be determined by hybridization of polynucleotides under conditions that form stable duplexes between homologous regions, followed by digestion with single-stranded-specific nuclease(s), and size determination of the digested fragments. Two DNA, or two polypeptide sequences are "substantially homologous" to each other when the sequences exhibit at least about 70%–85%, preferably at least about 85%–90%, more preferably at least about 90%–95%, and most preferably at least about 95%–98% sequence identity over a defined length of the molecules, or any percentage between the above-specified ranges, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

The degree of sequence identity between two nucleic acid molecules affects the efficiency and strength of hybridization events between such molecules. A partially identical nucleic acid sequence will at least partially inhibit a completely identical sequence from hybridizing to a target molecule. Inhibition of hybridization of the completely identical sequence can be assessed using hybridization assays that are well known in the art (e.g., Southern blot, Northern blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a target nucleic acid sequence, and then by selection of appropriate conditions the probe and the target sequence "selectively hybridize," or bind, to each other to form a hybrid molecule. A nucleic acid molecule that is capable of hybridizing selectively to a target sequence under "moderately stringent" typically hybridizes under conditions that allow detection of a target nucleic acid sequence of at least about 10–14 nucleotides in length having at least approximately 70% sequence identity with the sequence of the selected nucleic acid probe. Stringent hybridization conditions typically allow detection of target nucleic acid sequences of at least about 10–14 nucleotides in length having a sequence identity of greater than about 90–95% with the sequence of the selected nucleic acid probe. Hybridization conditions useful for probe/target hybridization where the probe and target have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.).

A "gene" as used in the context of the present invention is a sequence of nucleotides in a genetic nucleic acid (chromosome, plasmid, etc.) with which a genetic function is associated. A gene is a hereditary unit, for example of an organism, comprising a polynucleotide sequence that occupies a specific physical location (a "gene locus" or "genetic locus") within the genome of an organism. A gene can encode an expressed product, such as a polypeptide or a polynucleotide (e.g., tRNA). Alternatively, a gene may define a genomic location for a particular event/function, such as the binding of proteins and/or nucleic acids, wherein the gene does not encode an expressed product. Typically, a gene includes coding sequences, such as, polypeptide encoding sequences, and non-coding sequences, such as, promoter sequences, polyadenlyation sequences, transcriptional regulatory sequences (e.g., enhancer sequences). Many eucaryotic genes have "exons" (coding sequences) interrupted by "introns" (non-coding sequences). In certain cases, a gene may share sequences with another gene(s) (e.g., overlapping genes).

A "coding sequence" or a sequence which "encodes" a selected polypeptide, is a nucleic acid molecule which is transcribed (in the case of DNA) and translated (in the case of mRNA) into a polypeptide, for example, in vivo when placed under the control of appropriate regulatory sequences (or "control elements"). The boundaries of the coding sequence are typically determined by a start codon at the 5' (amino) terminus and a translation stop codon at the 3' (carboxy) terminus. A coding sequence can include, but is not limited to, cDNA from viral, procaryotic or eucaryotic mRNA, genomic DNA sequences from viral or procaryotic DNA, and even synthetic DNA sequences. A transcription termination sequence may be located 3' to the coding sequence. Other "control elements" may also be associated with a coding sequence. A DNA sequence encoding a polypeptide can be optimized for expression in a selected cell by using the codons preferred by the selected cell to represent the DNA copy of the desired polypeptide coding sequence. "Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence. Also encompassed are polypeptide sequences which are immunologically identifiable with a polypeptide encoded by the sequence.

Typical "control elements", include, but are not limited to, transcription promoters, transcription enhancer elements, transcription termination signals, polyadenylation sequences (located 3' to the translation stop codon), sequences for optimization of initiation of translation (located 5' to the coding sequence), translation enhancing sequences, and translation termination sequences. Transcription promoters can include inducible promoters (where expression of a polynucleotide sequence operably linked to the promoter is induced by an analyte, cofactor, regulatory protein, etc.), repressible promoters (where expression of a polynucleotide sequence operably linked to the promoter is induced by an analyte, cofactor, regulatory protein, etc.), and constitutive promoters. For purposes of the present invention, control elements for the dwf7 gene are found in the 5' and 3' UTRs shown in FIGS. 8A–8B, particularly at positions 43–142 and 1710–1890, respectively, of the figure. Control elements for HDF7 are found within the 5' and 3' UTRs shown in FIGS. 10A–10F, particularly within the region between positions 1–1505 and 2721–2925, respectively.

A control element, such as a promoter, "directs the transcription" of a coding sequence in a cell when RNA polymerase will bind the promoter and transcribe the coding sequence into mRNA, which is then translated into the polypeptide encoded by the coding sequence.

"Expression enhancing sequences" typically refer to control elements that improve transcription or translation of a polynucleotide relative to the expression level in the absence of such control elements (for example, promoters, promoter enhancers, enhancer elements, and translational enhancers (e.g., Shine and Delagarno sequences).

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence.

A "heterologous sequence" as used herein typically refers to a nucleic acid sequence that is not normally found in the cell or organism of interest. For example, a DNA sequence encoding a polypeptide can be obtained from a plant cell and introduced into a bacterial cell. In this case the plant DNA sequence is "heterologous" to the native DNA of the bacterial cell.

The "native sequence" or "wild-type sequence" of a gene is the polynucleotide sequence that comprises the genetic locus corresponding to the gene, e.g., all regulatory and open-reading frame coding sequences required for expression of a completely functional gene product as they are present in the wild-type genome of an organism. The native sequence of a gene can include, for example, transcriptional promoter sequences, translation enhancing sequences, introns, exons, and poly-A processing signal sites. It is noted that in the general population, wild-type genes may include multiple prevalent versions that contain alterations in sequence relative to each other and yet do not cause a discernible pathological effect. These variations are designated "polymorphisms" or "allelic variations."

"Recombinant" as used herein to describe a nucleic acid molecule means a polynucleotide of genomic, cDNA, semi-synthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide.

By "vector" is meant any genetic element, such as a plasmid, phage, transposon, cosmid, chromosome, virus etc., which is capable of transferring gene sequences to target cells. Generally, a vector is capable of replication when associated with the proper control elements. Thus, the term includes cloning and expression vehicles, as well as viral vectors and integrating vectors.

As used herein, the term "expression cassette" refers to a molecule comprising at least one coding sequence operably linked to a control sequence which includes all nucleotide sequences required for the transcription of cloned copies of the coding sequence and the translation of the mRNAs in an appropriate host cell. Such expression cassettes can be used to express eukaryotic genes in a variety of hosts such as bacteria, blue-green algae, plant cells, yeast cells, insect cells and animal cells. Under the invention, expression cassettes can include, but are not limited to, cloning vectors, specifically designed plasmids, viruses or virus particles. The cassettes may further include an origin of replication for autonomous replication in host cells, selectable markers, various restriction sites, a potential for high copy number and strong promoters.

A cell has been "transformed" by an exogenous polynucleotide when the polynucleotide has been introduced inside the cell. The exogenous polynucleotide may or may not be integrated (covalently linked) into chromosomal DNA making up the genome of the cell. In procaryotes and yeasts, for example, the exogenous DNA may be maintained on an episomal element, such as a plasmid. With respect to eucaryotic cells, a stably transformed cell is one in which the exogenous DNA has become integrated into the chromosome so that it is inherited by daughter cells through chromosome replication. This stability is demonstrated by the ability of the eucaryotic cell to establish cell lines or clones comprised of a population of daughter cells containing the exogenous DNA.

"Recombinant host cells," "host cells," "cells," "cell lines," "cell cultures," and other such terms denoting procaryotic microorganisms or eucaryotic cell lines cultured as unicellular entities, are used interchangeably, and refer to cells which can be, or have been, used as recipients for recombinant vectors or other transfer DNA, and include the progeny of the original cell which has been transfected. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

The term "dwf7 polynucleotide" refers to a polynucleotide derived from, or homologous to, the dwf7 gene. The gene encodes the protein variously referred to herein as DWF7, STE1 and DWF7/STE1. DWF7 is a $\Delta^7$sterol C-5 desaturase that functions in the brassinolide (BL) biosynthetic pathway from squalene to BL (see, FIG. 1). The dwf7 polynucleotide sequence and corresponding amino acid sequence are known and have been described in, e.g., Gachotte et al. (1996) Plant J. 9:391–398 and GenBank accession No. AF105034. See, also, FIGS. 8A–8D depicting the dwf7 gene sequence and the corresponding DWF7 amino acid sequence. As shown in FIGS. 8A–8D, the dwf7 gene spans the region from nucleotide positions 1–1889; the upstream 5' UTR, including the promoter region, spans nucleotide positions 1–142; the downstream 3' UTR is present from nucleotide position 1710–1889. The term as used herein encompasses a polynucleotide including a native sequence depicted in FIGS. 8A–8D, as well as modifications and fragments thereof.

The term encompasses alterations to the polynucleotide sequence, so long as the alteration results in a plant displaying one or more dwf7 phenotypic traits (described below) when the polynucleotide is expressed in a plant. Such modifications typically include deletions, additions and substitutions, to the native dwf7 sequence, so long as the mutation results in a plant displaying a dwf7 phenotype as defined below. These modifications may be deliberate, as through site-directed mutagenesis, or may be accidental, such as through mutations of plants which express the dwf7 polynucleotide or errors due to PCR amplification. The term encompasses expressed allelic variants of the wild-type dwf7 sequence which may occur by normal genetic variation or are produced by genetic engineering methods and which result in a detectable change in the wild-type dwf7 phenotype. Two particular dwf7 allelic variants described herein are dwf7-1 and dwf7-2. Polypeptides corresponding to these variants include about amino acids 1–60 and 1–230, respectively, of FIG. 9. However, the boundaries of these polypeptides may vary by 1 to 10 or more amino acids, or any integer therebetween. Thus, dwf7-1 and dwf7-2 polypeptides may include, for example, amino acids 1–59 and 1–229, respectively, or 3–62 and 3–232, respectively, and so on. Also described herein is a dwf7 polynucleotide termed "HDF7." The term "dwf7 polynucleotide" as used herein, is intended to encompass the HDF7 polynucleotide. This polynucleotide is shown in FIGS. 10A–10F herein. The polypeptide encoded by HDF7 is depicted at about positions 1–279 of FIG. 11. As with the dwf7-1 and dwf7-2 polypeptides, the boundaries of the HDF7 polypeptide may also vary by 1 to 10 or more amino acids, or any integer therebetween. These molecules are discussed in detail below.

The term "dwf7 phenotype" as used herein refers to any microscopic or macroscopic change in structure or morphology of a plant, such as a transgenic plant, as well as biochemical differences, which are characteristic of a dwf7 plant, compared to a progenitor, wild-type plant cultivated under the same conditions. Generally, morphological differences include short robust stems, reduced fertility, prolonged life cycle, dark-green, round, and curled leaves when grown in the light. In the dark, these plants exhibit short hypocotyls and expanded cotyledons, as compared to the wild-type plant. The height of such plants will typically be 75% or less of the wild-type plant, more typically 50% or less of the wild-type plant, and even more typically 25% or less of the wild-type plant, or any integer in between. Additional phenotypic morphological attributes of the dwf7 mutant are summarized in Table 1 of the examples. Biochemically, dwf7 hypocotyls are converted to wild-type length with the application of BL.

A "polypeptide" is used in it broadest sense to refer to a compound of two or more subunit amino acids, amino acid analogs, or other peptidomimetics. The subunits may be linked by peptide bonds or by other bonds, for example ester, ether, etc. As used herein, the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is typically called a polypeptide or a protein. Full-length proteins, analogs, and fragments thereof are encompassed by the definition. The terms also include postexpression modifications of the polypeptide, for example, glycosylation, acetylation, phosphorylation and the like. Furthermore, as ionizable amino and carboxyl groups are present in the molecule, a particular polypeptide may be obtained as an acidic or basic salt, or in neutral form. A polypeptide may be obtained directly from the source organism, or may be recombinantly or synthetically produced (see further below).

A "DWF7" polypeptide is a polypeptide as defined above, which is derived from a $\Delta^7$sterol C-5 desaturase that functions in the brassinolide (BL) biosynthetic pathway from squalene to BL (see, FIG. 1). The native sequence of full-length DWF7 is shown in FIG. 9. However, the term encompasses analogs and fragments of the native sequence so long as the protein functions for its intended purpose. Moreover, the term "DWF7 polypeptide" is intended to encompass the HDF7 polypeptide and analogs thereof.

The term "DWF7 analog" refers to derivatives of DWF7 and HDF7, or fragments of such derivatives, that retain desired function, e.g., as measured in assays as described further below. In general, the term "analog" refers to compounds having a native polypeptide sequence and structure with one or more amino acid additions, substitutions (generally conservative in nature) and/or deletions, relative to the native molecule, so long as the modifications do not destroy desired activity. Preferably, the analog has at least the same activity as the native molecule. Methods for making polypeptide analogs are known in the art and are described further below.

Particularly preferred analogs include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. It is to be understood that the terms include the various sequence polymorphisms that exist, wherein amino acid substitutions in the protein sequence do not affect the essential functions of the protein.

By "purified" and "isolated" is meant, when referring to a polypeptide or polynucleotide, that the molecule is separate and discrete from the whole organism with which the molecule is found in nature; or devoid, in whole or part, of sequences normally associated with it in nature; or a sequence, as it exists in nature, but having heterologous sequences (as defined below) in association therewith. It is to be understood that the term "isolated" with reference to a polynucleotide intends that the polynucleotide is separate and discrete from the chormosome from which the polynucleotide may derive. The term "purified" as used herein preferably means at least 75% by weight, more preferably at least 85% by weight, more preferably still at least 95% by weight, and most preferably at least 98% by weight, of biological macromolecules of the same type are present. An "isolated polynucleotide which encodes a particular polypeptide" refers to a nucleic acid molecule which is substantially free of other nucleic acid molecules that do not encode the subject polypeptide; however, the molecule may include some additional bases or moieties which do not deleteriously affect the basic characteristics of the composition.

By "fragment" is intended a polypeptide or polynucleotide consisting of only a part of the intact sequence and structure of the reference polypeptide or polynucleotide, respectively. The fragment can include a 3' or C-terminal deletion or a 5' or N-terminal deletion, or even an internal deletion, of the native molecule. A polynucleotide fragment of a dwf7 sequence will generally include at least about 15 contiguous bases of the molecule in question, more preferably 18–25 contiguous bases, even more preferably 30–50 or more contiguous bases of the dwf7 molecule, or any integer between 15 bases and the full-length sequence of the molecule. Fragments which provide at least one dwf7 phenotype as defined above are useful in the production of transgenic plants. Fragments are also useful as oligonucleotide probes, to find additional dwf7 sequences.

Similarly, a polypeptide fragment of a DWF7 molecule will generally include at least about 10 contiguous amino acid residues of the full-length molecule, preferably at least about 15–25 contiguous amino acid residues of the full-length molecule, and most preferably at least about 20–50 or more contiguous amino acid residues of the full-length DWF7 molecule, or any integer between 10 amino acids and the full-length sequence of the molecule. Such fragments are useful for the production of antibodies and the like.

By "transgenic plant" is meant a plant into which one or more exogenous polynucleotides have been introduced. Examples of means by which this can be accomplished are described below, and include Agrobacterium-mediated transformation, biolistic methods, electroporation, and the like. In the context of the present invention, the transgenic plant contains a polynucleotide which is not normally present in the corresponding wild-type plant and which confers at least one dwf7 phenotypic trait to the plant. The transgenic plant therefore exhibits altered structure, morphology or biochemistry as compared with a progenitor plant which does not contain the transgene, when the transgenic plant and the progenitor plant are cultivated under similar or equivalent growth conditions. Such a plant containing the exogenous polynucleotide is referred to here as an $R_1$ generation transgenic plant. Transgenic plants may also arise from sexual cross or by selfing of transgenic plants into which exogenous polynucleotides have been introduced. Such a plant containing the exogenous nucleic acid is also referred to here as an $R_1$ generation transgenic plant. Transgenic plants which arise from a sexual cross with another parent line or by selfing are "descendants or the progeny" of a $R_1$ plant and are generally called $F_n$ plants or $S_n$ plants, respectively, n meaning the number of generations.

II. Modes of Carrying Out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of compositions and methods similar or equivalent to those described herein can be used in the practice of the present invention, the preferred materials and methods are described herein.

The present invention is based on the morphological, biochemical, and molecular analysis of Arabidopsis dwf7 mutants. Morphologically, dwf7 plants display a dramatic reduction in the length of many different organs examined, and this size reduction is attributable to a defect in cell elongation. Biochemically, dwf7 hypocotyls are converted to wild-type length with the application of BL, suggesting a deficiency in BRs. In agreement with this, BR intermediate feeding analysis, accompanied by analysis of endogenous levels of BRs and sterols by using GC-SIM, indicates that dwf7 is defective specifically in the $\Delta^7$ sterol C-5 desaturase step of the sterol biosynthetic pathway. Sequencing of the $\Delta^7$ sterol C-5 desaturase gene in two allelic variants, dwf7-1 and dwf7-2, revealed premature stop codons, suggesting loss-of-function mutations. Thus, it appears that a shortage of sterols leads to a drastic reduction of BR levels in dwf7 mutants and to the characteristic dwarf phenotype.

The molecules of the present invention are therefore useful in the production of transgenic plants which display at least one dwf7 phenotype, so that the resulting plants have altered structure or morphology. The present invention particularly provides for altered structure or morphology such as reduced cell length, extended flowering periods, increased size of leaves or fruit, increased branching, increased seed production and altered sterol composition relative wild-type plants. The DWF7 polypeptides can be expressed to engineer a plant with desirable properties. The engineering is accomplished by transforming plants with nucleic acid constructs described herein which may also comprise promoters and secretion signal peptides. The transformed plants or their progenies are screened for plants that express the desired polypeptide.

Engineered plants exhibiting the desired altered structure or morphology can be used in plant breeding or directly in agricultural production or industrial applications. Plants having the altered polypeptide can be crossed with other altered plants engineered with alterations in other growth modulation enzymes, proteins or polypeptides to produce lines with even further enhanced altered structural morphology characteristics compared to the parents or progenitor plants.

Isolation of Nucleic Acid Sequences from Plants

The isolation of dwf7 sequences from the polynucleotides of the invention may be accomplished by a number of techniques. For instance, oligonucleotide probes based on the sequences disclosed here can be used to identify the desired gene in a cDNA or genomic DNA library from a desired plant species. To construct genomic libraries, large segments of genomic DNA are generated by random fragmentation, e.g. using restriction endonucleases, and are ligated with vector DNA to form concatemers that can be packaged into the appropriate vector. To prepare a library of tissue-specific cDNAs, mRNA is isolated from tissues and a cDNA library which contains the gene transcripts is prepared from the mRNA.

The cDNA or genomic library can then be screened using a probe based upon the sequence of a cloned gene such as the polynucleotides disclosed here. Probes may be used to hybridize with genomic DNA or cDNA sequences to isolate homologous genes in the same or different plant species. Alternatively, the nucleic acids of interest can be amplified from nucleic acid samples using amplification techniques. For instance, polymerase chain reaction (PCR) technology to amplify the sequences of the genes directly from mRNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Appropriate primers and probes for identifying dwf7-specific genes from plant tissues are generated from comparisons of the sequences provided herein. For a general overview of PCR see Innis et al. eds, *PCR Protocols: A Guide to Methods and Applications*, Academic Press, San Diego (1990). Appropriate primers for this invention include, for instance, those primers described in the Examples and Sequence Listings, as well as other primers derived from the dwf sequences disclosed herein. Suitable amplifications conditions may be readily determined by one of skill in the art in view of the teachings herein, for example, including reaction components and amplification conditions as follows: 10 mM Tris-HCl, pH 8.3, 50 mM potassium chloride, 1.5 mM magnesium chloride, 0.001% gelatin, 200 μM dATP, 200 μM dCTP, 200 μM dGTP, 200 μM dTTP, 0.4 μM primers, and 100 units per mL Taq polymerase; 96° C. for 3 min., 30 cycles of 96° C. for 45 seconds, 50° C. for 60 seconds, 72° C. for 60 seconds, followed by 72° C. for 5 min.

Polynucleotides may also be synthesized by well-known techniques as described in the technical literature. See, e.g., Carruthers, et al. (1982) *Cold Spring Harbor Symp. Quant. Biol.* 47:411–418, and Adams, et al. (1983) *J. Am. Chem. Soc.* 105:661. Double stranded DNA fragments may then be obtained either by synthesizing the complementary strand and annealing the strands together under appropriate conditions, or by adding the complementary strand using DNA polymerase with an appropriate primer sequence.

The polynucleotides of the present invention may also be used to isolate or create other mutant cell gene alleles. Mutagenesis consists primarily of site-directed mutagenesis followed by phenotypic testing of the altered gene product. Some of the more commonly employed site-directed mutagenesis protocols take advantage of vectors that can provide single stranded as well as double stranded DNA, as needed. Generally, the mutagenesis protocol with such vectors is as follows. A mutagenic primer, i.e., a primer complementary to the sequence to be changed, but consisting of one or a small number of altered, added, or deleted bases, is synthesized. The primer is extended in vitro by a DNA polymerase and, after some additional manipulations, the now double-stranded DNA is transfected into bacterial cells. Next, by a variety of methods, the desired mutated DNA is identified, and the desired protein is purified from clones containing the mutated sequence. For longer sequences, additional cloning steps are often required because long inserts (longer than 2 kilobases) are unstable in those vectors. Protocols are known to one skilled in the art and kits for site-directed mutagenesis are widely available from biotechnology supply companies, for example from Amersham Life Science, Inc. (Arlington Heights, Ill.) and Stratagene Cloning Systems (La Jolla, Calif.).

Control Elements

Regulatory regions can be isolated from the dwf7 gene and used in recombinant constructs for modulating the expression of the dwf7 gene or a heterologous gene in vitro and/or in vivo. As shown in FIGS. 8A–8D, the coding region of the dwf7 gene (designated by the light grey bar) begins at nucleotide position 143. The region of the gene spanning nucleotide positions 1–142 of FIGS. 8A–8D includes the dwf7 promoter. This region may be used in its entirety or fragments of the region may be isolated which provide the ability to direct expression of a coding sequence linked thereto.

Thus, promoters can be identified by analyzing the 5' sequences of a genomic clone corresponding to the dwf7-specific genes described here. Sequences characteristic of promoter sequences can be used to identify the promoter. Sequences controlling eukaryotic gene expression have been extensively studied. For instance, promoter sequence elements include the TATA box consensus sequence (TATAAT), which is usually 20 to 30 base pairs upstream of the transcription start site. In most instances the TATA box is required for accurate transcription initiation. In plants, further upstream from the TATA box, at positions –80 to –100, there is typically a promoter element with a series of adenines surrounding the trinucleotide G (or T) N G. (See, J. Messing et al., in *Genetic Engineering in Plants*, pp. 221–227 (Kosage, Meredith and Hollaender, eds. (1983)). Methods for identifying and characterizing promoter regions in plant genomic DNA are described, for example, in Jordano et al. (1989) *Plant Cell* 1:855–866; Bustos et al. (1989) *Plant Cell* 1:839–854; Green et al. (1988) *EMBO J.* 7:4035–4044; Meier et al. (1991) *Plant Cell* 3:309–316; and Zhang et al. (1996) *Plant Physiology* 110:1069–1079).

Additionally, the promoter region may include nucleotide substitutions, insertions or deletions that do not substantially affect the binding of relevant DNA binding proteins and hence the promoter function. It may, at times, be desirable to decrease the binding of relevant DNA binding proteins to "silence" or "down-regulate" a promoter, or conversely to increase the binding of relevant DNA binding proteins to "enhance" or "up-regulate" a promoter. In such instances, the nucleotide sequence of the promoter region may be modified by, e.g., inserting additional nucleotides, changing the identity of relevant nucleotides, including use of chemically-modified bases, or by deleting one or more nucleotides.

Promoter function can be assayed by methods known in the art, preferably by measuring activity of a reporter gene operatively linked to the sequence being tested for promoter function. Examples of reporter genes include those encoding luciferase, green fluorescent protein, GUS, neo, cat and bar.

Figure 6:
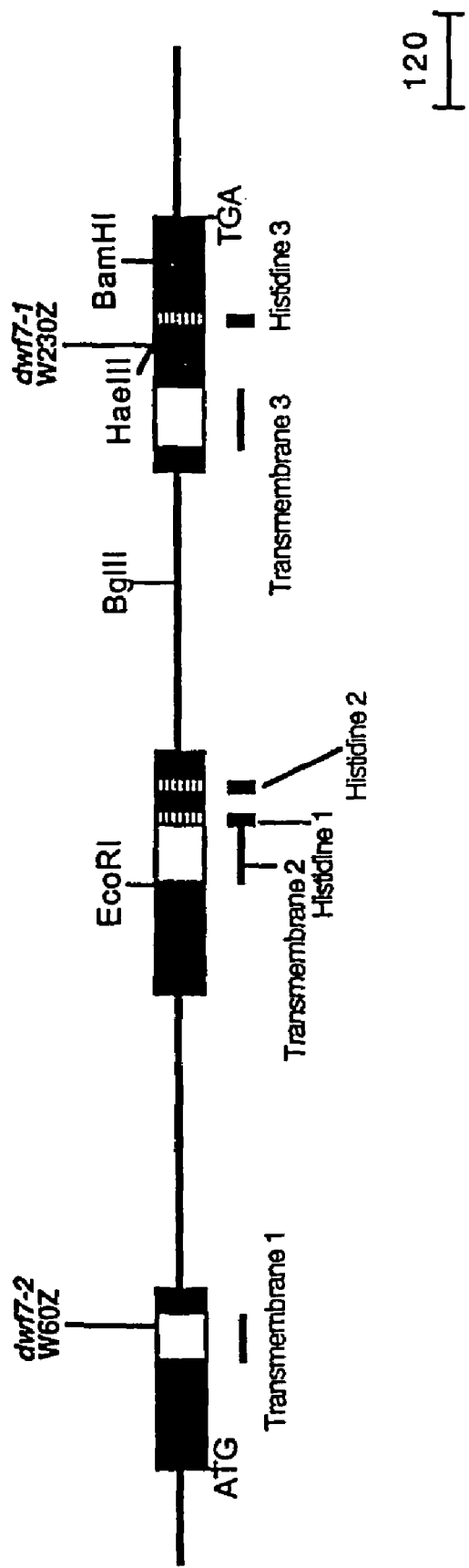
FIG. 6 is a schematic representation of the STE1 gene. Comparison of cDNA and genomic DNA sequences revealed three exons (thick boxes) and two introns (horizontal bars). The single open reading frame encodes a protein of 281 amino acids. The dwf7-2 (ste1-3) mutation is located in the first exon, changing a tryptophan to a stop codon. The dwf7-1 (ste1-2) mutation also changes a tryptophan to a stop codon (amino acid position 230). The three white boxes indicate the transmembrane domains, and the three histidine boxes are lightly shadowed. The figure is drawn to scale by using the GCK software (Textco, Inc., West Lebanon, N.H.). Bar=120 bp.

Polynucleotides comprising untranslated (UTR) sequences and intron/exon junctions are also within the scope of the invention. UTR sequences include introns and 5' or 3' untranslated regions (5' UTRs or 3' UTRs). As shown in FIG. 6, the dwf7 gene sequence includes three exons (thick boxes) and two introns (horizontal bars). See, also, FIGS. 8A–8D for the 5' and 3' UTRs. Similarly, the HDF7 gene includes three exons (at positions 1506–1734, 2024–2329 and 2416–2720, denoted by the corresponding protein sequence indicated) and two introns (between these exons) and 5' and 3' UTRs. These portions of the dwf7 and HDF7 genes especially UTRs, can have regulatory functions related to, for example, translation rate and mRNA stability. Thus, these portions of the gene can be isolated for use as elements of gene constructs for expression of polynucleotides encoding desired polypeptides.

Introns of genomic DNA segments may also have regulatory functions. Sometimes promoter elements, especially transcription enhancer or suppressor elements, are found within introns. Also, elements related to stability of heteronuclear RNA and efficiency of transport to the cytoplasm for translation can be found in intron elements. Thus, these segments can also find use as elements of expression vectors intended for use to transform plants.

The introns, UTR sequences and intron/exon junctions can vary from the native sequence. Such changes from those sequences preferably will not affect the regulatory activity of the UTRs or intron or intron/exon junction sequences on expression, transcription, or translation. However, in some instances, down-regulation of such activity may be desired to modulate traits or phenotypic or in vitro activity.

Use of Nucleic Acids of the Invention to Inhibit Gene Expression

The isolated sequences prepared as described herein, can be used to prepare expression cassettes useful in a number of techniques. For example, expression cassettes of the invention can be used to suppress endogenous dwf7 gene expression. Inhibiting expression can be useful, for instance, in suppressing the phenotype (e.g., dwarf appearance, the $\Delta^7$ sterol C-5 desaturase activity) exhibited by dwf7 plants.

A number of methods can be used to inhibit gene expression in plants. For instance, antisense technology can be conveniently used. To accomplish this, a nucleic acid segment from the desired gene is cloned and operably linked to a promoter such that the antisense strand of RNA will be transcribed. The expression cassette is then transformed into plants and the antisense strand of RNA is produced. In plant cells, it has been suggested that antisense RNA inhibits gene expression by preventing the accumulation of mRNA which encodes the enzyme of interest, see, e.g., Sheehy et al. (1988) *Proc. Nat. Acad. Sci. USA* 85:8805–8809, and Hiatt et al., U.S. Pat. No. 4,801,340.

The nucleic acid segment to be introduced generally will be substantially identical to at least a portion of the endogenous gene or genes to be repressed. The sequence, however, need not be perfectly identical to inhibit expression. The vectors of the present invention can be designed such that the inhibitory effect applies to other proteins within a family of genes exhibiting homology or substantial homology to the target gene.

For antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of at least about 500 nucleotides is especially preferred. It is to be understood that any integer between the above-recited ranges is intended to be captured herein.

Catalytic RNA molecules or ribozymes can also be used to inhibit expression of dwf7 genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes is described in Haseloff et al. (1988) Nature 334:585–591.

Another method of suppression is sense suppression. Introduction of expression cassettes in which a nucleic acid is configured in the sense orientation with respect to the promoter has been shown to be an effective means by which to block the transcription of target genes. For an example of the use of this method to modulate expression of endogenous genes see, Napoli et al. (1990) The Plant Cell 2:279–289 and U.S. Pat. Nos. 5,034,323, 5,231,020, and 5,283,184.

Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. It is to be understood that any integer between the above-recited ranges is intended to be captured herein. As with antisense regulation, the effect should apply to any other proteins within a similar family of genes exhibiting homology or substantial homology.

For sense suppression, the introduced sequence in the expression cassette, needing less than absolute identity, also need not be full length, relative to either the primary transcription product or fully processed mRNA. This may be preferred to avoid concurrent production of some plants which are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used.

Use of Nucleic Acids of the Invention to Enhance Gene Expression

In addition to inhibiting certain features of a plant, the polynucleotides of the invention can be used to increase certain features such as extending flowering, producing larger leaves or fruit, producing increased branching and increasing seed production. This can be accomplished by the overexpression of dwf7 polynucleotides.

The exogenous dwf7 polynucleotides do not have to code for exact copies of the endogenous DWF7 and HDF7 proteins. Modified DWF7 and HDF7 protein chains can also be readily designed utilizing various recombinant DNA techniques well known to those skilled in the art and described for instance, in Sambrook et al., supra. Hydroxylamine can also be used to introduce single base mutations into the coding region of the gene (Sikorski et al. (1991) Meth. Enzymol. 194: 302–318). For example, the chains can vary from the naturally occurring sequence at the primary structure level by amino acid substitutions, additions, deletions, and the like. These modifications can be used in a number of combinations to produce the final modified protein chain.

Preparation of Recombinant Vectors

To use isolated sequences in the above techniques, recombinant DNA vectors suitable for transformation of plant cells are prepared. Techniques for transforming a wide variety of higher plant species are well known and described further below as well as in the technical and scientific literature. See, for example, Weising et al. (1988) Ann. Rev. Genet. 22:421–477. A DNA sequence coding for the desired polypeptide, for example a cDNA sequence encoding the full length DWF7 protein, will preferably be combined with transcriptional and translational initiation regulatory sequences which will direct the transcription of the sequence from the gene in the intended tissues of the transgenic plant.

Such regulatory elements include but are not limited to the promoters derived from the genome of plant cells (e.g., heat shock promoters such as soybean hsp 17.5-E or hsp 17.3-B (Gurley et al. (1986) Mol. Cell. Biol. 6:559–565); the promoter for the small subunit of RUBISCO (Coruzzi et al. (1984) EMBO J. 3:1671–1680; Broglie et al. (1984) Science 224:838–843); the promoter for the chlorophyll a/b binding protein) or from plant viruses viral promoters such as the 35S RNA and 19S RNA promoters of CaMV (Brisson et al. (1984) Nature 310:511–514), or the coat protein promoter of TMV (Takamatsu et al. (1987) EMBO J. 6:307–311), cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, heat shock promoters (e.g., as described above) and the promoters of the yeast alpha-mating factors.

In construction of recombinant expression cassettes of the invention, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the T-DNA mannopine synthetase promoter (e.g., the 1'- or 2'-promoter derived from T-DNA of Agrobacterium tumafaciens), and other transcription initiation regions from various plant genes known to those of skill.

Alternatively, the plant promoter may direct expression of the polynucleotide of the invention in a specific tissue (tissue-specific promoters) or may be otherwise under more precise environmental control (inducible promoters). Examples of tissue-specific promoters under developmental control include promoters that initiate transcription only in certain tissues, such as fruit, seeds, or flowers such as tissue- or developmental-specific promoter, such as, but not limited to the cell promoter, the CHS promoter, the PATATIN promoter, etc. The tissue specific E8 promoter from tomato is particularly useful for directing gene expression so that a desired gene product is located in fruits.

Other suitable promoters include those from genes encoding embryonic storage proteins. Examples of environmental conditions that may affect transcription by inducible promoters include anaerobic conditions, elevated temperature, or the presence of light. If proper polypeptide expression is desired, a polyadenylation region at the 3'-end of the coding region should be included. The polyadenylation region can be derived from the natural gene, from a variety of other plant genes, or from T-DNA. In addition, the promoter itself can be derived from the dwf7 or HDF7 genes, as described above.

The vector comprising the sequences (e.g., promoters or coding regions) from genes of the invention will typically comprise a marker gene which confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosluforon or Basta.

Production of Transgenic Plants

DNA constructs of the invention may be introduced into the genome of the desired plant host by a variety of conventional techniques. For reviews of such techniques see, for example, Weissbach & Weissbach *Methods for Plant Molecular Biology* (1988, Academic Press, N.Y.) Section VIII, pp. 421–463; and Grierson & Corey, *Plant Molecular Biology* (1988, 2d Ed.), Blackie, London, Ch. 7–9. For example, the DNA construct may be introduced directly into the genomic DNA of the plant cell using techniques such as electroporation and microinjection of plant cell protoplasts, or the DNA constructs can be introduced directly to plant tissue using biolistic methods, such as DNA particle bombardment (see, e.g., Klein et al. (1987) *Nature* 327:70–73). Alternatively, the DNA constructs may be combined with suitable T-DNA flanking regions and introduced into a conventional Agrobacterium tumefaciens host vector. Agrobacterium tumefaciens-mediated transformation techniques, including disarming and use of binary vectors, are well described in the scientific literature. See, for example Horsch et al. (1984) *Science* 233:496–498, and Fraley et al. (1983) *Proc. Nat'l. Acad. Sci. USA* 80:4803. The virulence functions of the Agrobacterium tumefaciens host will direct the insertion of the construct and adjacent marker into the plant cell DNA when the cell is infected by the bacteria using binary T DNA vector (Bevan (1984) *Nuc. Acid Res.* 12:8711–8721) or the co-cultivation procedure (Horsch et al. (1985) *Science* 227:1229–1231). Generally, the Agrobacterium transformation system is used to engineer dicotyledonous plants (Bevan et al. (1982) *Ann. Rev. Genet* 16:357–384; Rogers et al. (1986) *Methods Enzymol.* 118:627–641). The Agrobacterium transformation system may also be used to transform, as well as transfer, DNA to monocotyledonous plants and plant cells. (see Hernalsteen et al. (1984) *EMBO J* 3:3039–3041; Hooykass-Van Slogteren et al. (1984) *Nature* 311:763–764; Grimsley et al. (1987) *Nature* 325:1677–179; Boulton et al. (1989) *Plant Mol. Biol.* 12:31–40; and Gould et al. (1991) *Plant Physiol.* 95:426–434).

Alternative gene transfer and transformation methods include, but are not limited to, protoplast transformation through calcium-, polyethylene glycol (PEG)- or electroporation-mediated uptake of naked DNA (see Paszkowski et al. (1984) *EMBO J.* 3:2717–2722, Potrykus et al. (1985) *Molec. Gen. Genet.* 199:169–177; Fromm et al. (1985) *Proc. Nat. Acad. Sci. USA* 82:5824–5828; and Shimamoto (1989) *Nature* 338:274–276) and electroporation of plant tissues (D'Halluin et al. (1992) *Plant Cell* 4:1495–1505). Additional methods for plant cell transformation include microinjection, silicon carbide mediated DNA uptake (Kaeppler et al. (1990) *Plant Cell Reporter* 9:415–418), and microprojectile bombardment (see Klein et al. (1988) *Proc. Nat. Acad. Sci. USA* 85:4305–4309; and Gordon-Kamm et al. (1990) *Plant Cell* 2:603–618).

Transformed plant cells which are produced by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., "Protoplasts Isolation and Culture" in *Handbook of Plant Cell Culture*, pp. 124–176, Macmillian Publishing Company, New York, 1983; and Binding, *Regeneration of Plants, Plant Protoplasts*, pp. 21–73, CRC Press, Boca Raton, 1985. Regeneration can also be obtained from plant callus, explants, organs, pollens, embryos or parts thereof. Such regeneration techniques are described generally in Klee et al. (1987) *Ann. Rev. of Plant Phys.* 38:467–486.

The nucleic acids of the invention can be used to confer desired traits on essentially any plant. A wide variety of plants and plant cell systems may be engineered for the desired physiological and agronomic characteristics described herein using the nucleic acid constructs of the present invention and the various transformation methods mentioned above. In preferred embodiments, target plants and plant cells for engineering include, but are not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., petunia, rose, chrysanthemum), conifers and pine trees (e.g., pine fir, spruce); plants used in phytoremediation (e.g., heavy metal accumulating plants); oil crops (e.g., sunflower, rape seed) and plants used for experimental purposes (e.g., Arabidopsis). Thus, the invention has use over a broad range of plants, including, but not limited to, species from the genera Asparagus, Avena, Brassica, Citrus, Citrullus, Capsicum, Cucurbita, Daucus, Glycine, Hordeum, Lactuca, Lycopersicon, Malus, Manihot, Nicotiana, Oryza, Persea, Pisum, Pyrus, Prunus, Raphanus, Secale, Solanum, Sorghum, Triticum, Vitis, Vigna, and Zea.

One of skill in the art will recognize that after the expression cassette is stably incorporated in transgenic plants and confirmed to be operable, it can be introduced into other plants by sexual crossing. Any of a number of standard breeding techniques can be used, depending upon the species to be crossed.

A transformed plant cell, callus, tissue or plant may be identified and isolated by selecting or screening the engineered plant material for traits encoded by the marker genes present on the transforming DNA. For instance, selection may be performed by growing the engineered plant material on media containing an inhibitory amount of the antibiotic or herbicide to which the transforming gene construct confers resistance. Further, transformed plants and plant cells may also be identified by screening for the activities of any visible marker genes (e.g., the β-glucuronidase, luciferase, B or C1 genes) that may be present on the recombinant nucleic acid constructs of the present invention. Such selection and screening methodologies are well known to those skilled in the art.

Physical and biochemical methods also may be used to identify plant or plant cell transformants containing the gene constructs of the present invention. These methods include but are not limited to: 1) Southern analysis or PCR amplification for detecting and determining the structure of the recombinant DNA insert; 2) Northern blot, S1 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) protein gel electrophoresis, Western blot techniques, immunoprecipitation, or enzyme-linked immunoassays, where the gene construct products are proteins. Additional techniques, such as in situ hybridization, enzyme staining, and immunostaining, also may be used to detect the presence or expression of the recombinant construct in specific plant organs and tissues. The methods for doing all these assays are well known to those skilled in the art.

Effects of gene manipulation using the methods of this invention can be observed by, for example, northern blots of the RNA (e.g., mRNA) isolated from the tissues of interest. Typically, if the amount of mRNA has increased, it can be assumed that the endogenous dwf7 gene is being expressed at a greater rate than before. Other methods of measuring DWF7 activity can be used. For example, cell length can be measured at specific times. Because dwf7 affects the BR biosynthetic pathway, an assay that measures the amount of BL can also be used. Such assays are known in the art. Different types of enzymatic assays can be used, depending on the substrate used and the method of detecting the increase or decrease of a reaction product or by-product. In addition, the levels of DWF7 protein expressed can be measured immunochemically, i.e., ELISA, RIA, EIA and other antibody based assays well known to those of skill in the art, by electrophoretic detection assays (either with staining or western blotting), and sterol (BL) detection assays.

The transgene may be selectively expressed in some tissues of the plant or at some developmental stages, or the transgene may be expressed in substantially all plant tissues, substantially along its entire life cycle. However, any combinatorial expression mode is also applicable.

The present invention also encompasses seeds of the transgenic plants described above wherein the seed has the transgene or gene construct. The present invention further encompasses the progeny, clones, cell lines or cells of the transgenic plants described above wherein said progeny, clone, cell line or cell has the transgene or gene construct.

Polypeptides

The present invention also includes DWF7 polypeptides, including such polypeptides as a fusion, or chimeric protein product (comprising the protein, fragment, analog, mutant or derivative joined via a peptide bond to a heterologous protein sequence (of a different protein)). Such a chimeric product can be made by ligating the appropriate nucleic acid sequences encoding the desired amino acid sequences to each other by methods known in the art, in the proper coding frame, and expressing the chimeric product by methods commonly known in the art.

In addition, DWF7 polypeptides, derivatives (including fragments and chimeric proteins), mutants and analogues can be chemically synthesized. See, e.g., Clark-Lewis et al. (1991) Biochem. 30:3128–3135 and Merrifield (1963) J. Amer. Chem. Soc. 85:2149–2156. For example, DWF7, derivatives, mutants and analogs can be synthesized by solid phase techniques, cleaved from the resin, and purified by preparative high performance liquid chromatography (e.g., see Creighton, 1983, Proteins, Structures and Molecular Principles, W. H. Freeman and Co., N.Y., pp. 50–60). DWF7, derivatives and analog that are proteins can also be synthesized by use of a peptide synthesizer. The composition of the synthetic peptides may be confirmed by amino acid analysis or sequencing (e.g., the Edman degradation procedure; see Creighton, 1983, Proteins, Structures and Molecular Principles, W. H. Freeman and Co., N.Y., pp. 34–49).

Applications

The present invention finds use in various applications, for example, including but not limited to those listed above.

The polynucleotide sequences may additionally be used to isolate mutant dwf7 gene alleles. Such mutant alleles may be isolated from plant species either known or proposed to have a genotype which contributes to altered plant morphology. Additionally, such plant dwf7 gene sequences can be used to detect plant dwf7 gene regulatory (e.g., promoter or promotor/enhancer) defects which can affect plant growth.

The molecules of the present invention can be used to provide plants with increased seed and/or fruit production, extended flowering periods and increased branching. The molecules described herein can be used to alter the sterol composition of a plant, thereby increasing or reducing cholesterol content in the plant. A still further utility of the molecules of the present invention is to provide a tool for studying the biosynthesis of brassinosteriods, both in vitro and in vivo.

The dwf7 gene of the invention also has utility as a transgene encoding a the $\Delta^7$ sterol C-5 desaturation protein that mediates one or more steps in brassinosteriod biosynthesis which results in a transgenic plant to alter plant structure or morphology. The dwf7 gene also has utility for encoding the DWF7 protein in recombinant vectors which may be inserted into host cells to express the DWF7 protein. Further, the dwf7 polynucleotides of the invention may be utilized (1) as nucleic acid probes to screen nucleic acid libraries to identify other enzymatic genes or mutants; (2) as nucleic acid sequences to be mutated or modified to produce DWF7 protein variants or derivatives; (3) as nucleic acids encoding the $\Delta^7$ sterol C-5 desaturases in molecular biology techniques or industrial applications commonly known to those skilled in the art.

The dwf7 nucleic acid molecules may be used to design antisense molecules, useful, for example, in gene regulation or as antisense primers in amplification reactions of dwf7 gene nucleic acid sequences. With respect to dwf7 gene regulation, such techniques can be used to regulate, for example, plant growth, development or gene expression. Further, such sequences may be used as part of ribozyme and/or triple helix sequences, also useful for dwf7 gene regulation.

The dwf7 control element (e.g., promoter) of the present invention may be utilized as a plant promoter to express any protein, polypeptide or peptide of interest in a transgenic plant. In particular, the dwf7 promoter may be used to express a protein involved in brassinosteriod biosynthesis.

The Arabidopsis DWF7 protein of the invention can be used in any biochemical applications (experimental or industrial) where $\Delta^7$ sterol C-5 desaturation activity is desired, for example, but not limited to, regulation of BL synthesis, regulation of other sterol synthesis, modification of elongating plant structures, and experimental or industrial biochemical applications known to those skilled in the art.

III. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Restriction and modifying enzymes, as well as PCR reagents were purchased from commercial sources, and used according to the manufacturers' directions. In the cloning of DNA fragments, except where noted, all DNA manipulations were done according to standard procedures. See, e.g., Sambrook et al., supra. Restriction enzymes, $T_4$ DNA ligase, *E. coli*, DNA polymerase I, Klenow fragment, and other biological reagents were purchased from commercial suppliers and used according to the manufacturers' directions.

Materials and Methods

A. Plant Growth

For sterile growth of *Arabidopsis thaliana* plants, seeds of mutants and the wild type were sterilized (50% Clorox and 0.005% Triton X-100) for 8 min, washed three times with sterile distilled water, and dried with 95% ethanol. The seeds were sprinkled on 0.8% agar-solidified media or in liquid media containing 1× Murashige and Skoog (Murashige and Skoog (1962) Physiol. Plant. 15:473–497) salts and 0.5% sucrose (pH 5.8 with KOH). For the plants grown in the dark, the seeds on the plates were illuminated for 3 hr (240 µmol m$^{-2}$ sec$^{-1}$) before being wrapped with two or three layers of aluminum foil. For the mature plants used for morphometric analysis and gas chromatography-selective ion monitoring (GC-SIM) studies, seeds were planted on soil (Metromix 350; Grace Sierra Co., Milpitas, Calif.) presoaked with distilled water. The flats containing the pots were covered with plastic wrap and cold-treated at 4° C. for 2 days before transfer to a growth chamber (16 hr of light [240 µmol m$^{-2}$ sec$^{-1}$] and 8 hr of dark at 22 and 21° C., respectively, and 75 to 90% humidity). The plastic wrap was removed after 2 to 3 days. The pots were subirrigated in distilled water or Hoagland's nutrient solution as required.

B. Morphometric and Physiological Analysis

At 5 weeks of age, the various morphological traits listed in Table 1 (below) were measured. The number of seeds per silique was determined after the plants were completely dried. Unopened siliques from each plant were selected and crushed, and the number of seeds was counted under a dissecting microscope. To measure the fresh and dry weight, the aerial parts of the plants were cut and immediately weighed to obtain the fresh weight; the plants were then completely dried in a 60° C. oven for 5 days before measuring the dry weight. Flowers were harvested immediately after petal opening. Observations on the structure of flowers were made with flowers at stage 14 (Smyth et al. (1990) Plant Cell 2:755–767), which are right beneath the cluster of developing flowers at the shoot apices. Individual organs of a flower were separated under the dissecting microscope. The length of the organs was measured to a tenth of a millimeter, and the four longest stamens for each flower were measured and the mean value calculated.

The anatomical studies using a scanning electronic microscope and a light microscope were performed as described by Azpiroz et al. (1998) Plant Cell 10:219–230.

C. Mapping and Sequencing of the DWARF7 Locus

The mapping of dwf7 was performed using simple sequence length polymorphism (SSLP) markers (Bell and Ecker (1994) Genomics 19:137–144). Briefly, dwf7-1 mutants (Wassilewskija-2 [Ws-2] background) were crossed to Columbia wild-type plants. Genomic DNA was isolated (Dellaporta et al. 1983) from individual $F_2$ dwarf plants. To locate the mutation to one of the five chromosomes, 20 individual plants were tested with at least two SSLP markers per chromosome. The polymerase chain reaction (PCR) amplified products were analyzed on 4% agarose gels in 1× TAE buffer (40 mM Tris-acetate and 10 mM EDTA). Once the dwf7-1 mutation was shown to be linked to the nga162 marker located on chromosome 3 (recombination ratio 11.9%), we tested marker nga172, which maps at 2.2 centimorgans. No recombination was detected between the dwf7-1 mutation and nga2 when 86 chromosomes were tested, suggesting that dwf7-1 is linked closely to the nga172 marker. Linkage between the markers and the dwarf phenotype was determined according to Koornneef and Stam (1992) Genetic analysis. In Methods in Arabidopsis Research, C. Koncz, N.-H. Chua, and J. Schell, eds (Singapore: World Scientific Publishing Co.), pp. 83–99.

PCR products amplified using primer sets derived from the cDNA sequence of STROLI (STE1) were subjected to sequencing. To design sets of primers that do not fall in exon-intron junctions, we predicted possible splice sites by using the RNASPL program available at the internet site of Baylor College of Medicine (Houston, Tex.; http://dot.imgen.bcm.tms.edu:9331/seq-searchlgene-search.html). Primers were designed using the Primer Selection software of DNAstar (DNASTAR Inc., Madison, Wis.). Oligonucleotide sequences 5' to 3' are CAGTGTGAGTAATTTAGCAT-TACTA (S5D_FF)(SEQ ID NO:1), GGAAAGATCAT-CAAACATTTACATGT(S5D_LR)(SEQ ID NO:2), GCG-CAATCTTCTTTCGTTT (S5D__1F)(SEQ ID NO:3), TGGACAACAACAACACAAGA (S5D__1R)(SEQ ID NO:4), GATGCACAGAGAGCT-TCATGAC (S5D__2F) (SEQ ID NO:5), CCGGCAAATGGAGAGAGTGTAT (S5D__2R)(SEQ ID NO:6, CACCCATCATATCTACAA-CAA(S5DF__3F)(SEQ ID NO:7), and CATCTTTTGCCG-GCGAATCTAT (S5D__4F)(SEQ ID NO:8)(underlines were added to distinguish forward or reverse primers from the gene acronym S5D). Primers were purchased from Genosys Biotechnologies, Inc. (The Woodlands, Tex.). For template DNA, genomic DNA was isolated from two or three leaves of dwf7-1 and wild-type plants according to the method described by Krysan et al. (1996) Proc. Natl. Acad. Sci. USA 93:8145–8150. Amplification of the DNA fragment spanning the whole coding region was performed with the S5D__4F and S5D__1R primer set with Taq polymerase (Boebringer Mannheim).

Standard PCR reaction mixtures, 1× PCR buffer (10 mM Tris-HCl, 1.5 mM MgCl$_2$, and 50 mM KCl, pH 8.3), 0.2 µM each of forward and reverse primer, 0.2 mM each deoxynucleotide triphosphates, 1 ng of genomic DNA, and 2 units of Taq polymerase were subjected to a PCR program consisting of an initial denaturation at 95° C. for 2 min and then for 35 cycles (95° C. for 30 sec, 56° C. for 30 sec, and 72° C. for 2.5 min), with a final elongation step of 7 min at 72° C. PCR-amplified DNA was size-separated on 0.8% agarose gels in 1×TAE, and the resulting DNA bands were gel-purified using a DNA purification kit (Bio-Rad). The concentration of the extracted DNA was measured by comparing the band intensity with a DNA mass standard (Bethesda Research Laboratories). Sequencing of the DNA was performed at the Arizona Research Laboratory (University of Arizona, Tucson). DNA sequence analysis was conducted using software packages, including one from Genetics Computer Group (Madison, Wis.) and other database search tools available on the Internet.

The base change in dwf7-1 eliminated the recognition site for a restriction enzyme HaeIII by converting the sequence from GGCC to AGCC. Thus, we utilized this polymorphism to test the cosegregation of the dwarf phenotype with the mutation. The 0.8 kb of DNA spanning the mutation was amplified using S5D_3F and S5D_1R primers from 17 different dwarf plants from the mapping lines. Two microliters from each 20 µL of PCR-amplified DNA was digested with the restriction enzyme HaeIII (Boehringer Mannheim). After complete digestion, the samples were resolved on a 2% agarose gel in 1× TAE buffer.

Genomic DNA sequence flanking the cDNA was identified by sequencing the products obtained from thermal asymmetric interlaced PCR (TAIL PCR)(Liu et al. (1995) Plant J. 8:457–463). Two sets of primers were used to amplify the 5' and 3' flanking DNA. Oligonucleotide sequences 5' to 3' are GTAGAAGCACCAGAGGAAAC-CGGAGATGAAGT (D7-5-1; melting temperature of 69° C.)(SEQ ID NO:9), AAGTATAGTAGGGTTCCGGC-GAGG-TA (D7-5-2; melting temperature of 64° C.)(SEQ ID NO:10), ATAGATTCGCCG-GCAAAAGATGACTC (D7-5-3, melting temperature of 63° C.)(SEQ ID NO:11), TGCAGGATACCATACGATACACCACACGACAT (D7-3-1; melting temperature of 68° C.)(SEQ ID NO:12), CAT-ACGATACACCACACGACATACAAGCAT-AACTA (D7-3-2; melting temperature of 67° C.)(SEQ ID NO:13), and ATATGGATG-GATTGGATGTTTGGCTCTC (D-7-3-3; melting temperature of 63° C.)(SEQ ID NO:14). The melting temperatures of each primer was calculated with the formula 69.3+0.41 (%GC)−650/L (Mazars et al. (1991) nucleic Acids Res. 19:4783), where L is length of primer. Arbitrary degenerate primers AD1, AD2, and AD3 were synthesized according to the sequence described by Liu et al.(1995) Plant J. 8:45 7–463. TAIL PCR was performed according to the program originally described by Liu et al. 1995. TAIL PCR-amplified DNA was separated on 1% agarose gels and gel extracted for sequencing.

D. Feeding Experiments

Biochemical complementation of dwf7-1 plants with different concentrations of brassinolide (BL) was performed in liquid media. BL-supplemented (control, $10^{-9}$, $10^{-8}$, and $10$ M) sterile liquid media (1.5 mL) was dispensed into wells of a 24-well plate (Corning Co., Corning, N.Y.). Three seedlings, germinated on agar-solidified media, were transferred into each well. After a week of growth with continuous shaking (230 rpm), the seedlings were lightly stained with toluidine blue, and hypocotyls and roots were measured to the nearest millimeter.

Feeding experiments using biosynthetic intermediates were performed with 3-week-old mutant plants. The intermediates tested were diluted to the desired concentration with water containing 0.01% Tween 20. Two microliters of each brassinosteroid (BR) solution was applied daily to the shoot tips of plants by using a micro pipettman. After 1 week of treatment, total growth of inflorescence and pedicels was measured to the nearest millimeter (n=15).

E. Analysis of Endogenous BRs

Plants were grown for 5 weeks on soil. Two hundred grams of the aerial parts of plants, including stems, flowers, leaves, and siliques, was harvested and subjected to BR extraction. The procedure for extraction and analysis of BR intermediates by using GC-SIM has been described (Fujioka et al. (1997) Plant Cell 9:1951–1962).

F. $^{13}$C-Labeled Mevalonic Acid Feeding Experiments

Before feeding experiments, seedlings were germinated and grown on 0.5× Murashige and Skoog (Murashige and Skoog (1962) Physiol. Plant. 15:473–497) agar medium in the light at 22° C. (25 mL per dish). Eight days after sowing, the seedlings were transferred to a 200-mL flask containing 30 mL of Murashige and Skoog (Murashige and Skoog (1962) Physiol. Plant. 15:473–497) media supplemented with 3% sucrose (Ws-2, five seedlings; dwf7-1, 40 seedlings).

Compactin (mevastatin; Sigma) was converted to its sodium salt as described previously (Kita et al. (1980) J. Clin. Invest. 66:1094–1100). DL-Mevalonolactone-2-$^{13}$C ($^{13}$C-MVA; Isotec, Miamisburg, Ohio) was dissolved in methanol. Solutions of compactin and $^{13}$C-MVA were added aseptically to each 200-mL flask (final concentration, 10 µM compactin and 4.5 mM $^{13}$C-MVA) just after the seedlings were transferred, and seedlings were allowed to grow for 11 days at 22° C. in the light on a shaker (110 rpm). After incubation, the seedlings (~5 g fresh weight of both Ws-2 and dwf7-1 plant materials) were extracted with methanol (250 mL), and the extract was partitioned between CHCl$_3$ and H$_2$O. The CHCl$_3$-soluble fraction was purified with a silica cartridge column (Sep-Pak Vac 12 cc; Waters, Milford, Mass.), which was eluted with 20 mL of CHCl$_3$. The eluate was purified with an octadecylsilane (ODS) cartridge column (Sep-Pak PLUS C18; Waters), which was eluted with 20 mL of methanol. The fraction was subjected to HPLC on an ODS column as follows: column, Senshu Pak ODS 4150-N (150×10 mm); solvent, methanol; flow rate, 2 mL/min; and detection, UV 205 nm. Fractions were collected every 0.5 min (between retention times of 10 to 20 min). Main fractions of each sterol were as follows: 5-dehydroepisterol (retention time of 11.5 to 12 min), episterol (retention time of 12.5 to 13 min), 24-methylenecholesterol (24-MC; retention time of 13 to 13.5 min), 7-dehydrocampestanol (retention time of 14.5 to 15 min), and campesterol (CR; retention time of 15.5 to 16 min).

Each fraction was converted to a trimethylsilyl derivative and analyzed by gas chromatography-mass spectrometry (GC-MS). GC-MS analyses were performed on a JEOL Automass JMS-AM 150 mass spectrometer (Tokyo, Japan) connected to a Hewlett-Packard 5890A-II gas chromatograph with a capillary column DB-5 (0.25 mm×15 m; 0.25-µm film thickness). The analytical conditions were the same as previously described (Fujioka et al. 1997).

5-Dehydroepisterol, episterol, and 7-dehydrocampestanol were chemically synthesized.

EXAMPLE 1

Isolation of dwf7 Mutants

The dwf7-1 mutant originally was identified in a screen of 14,000 T-DNA-transformed lines of Arabidopsis. Genetic complementation tests with other dwf loci indicated that dwf7 belongs to a unique complementation group. dwf7-1 segregated as a monogenic recessive mutation; progeny from a heterozygote segregated 325 (wild-type):98 (dwf7-1). Although dwf7-1 originated from a T-DNA mutant population, it failed to cosegregate with the kanamycin resistance marker in the T-DNA, suggesting that dwf7-1 was an untagged mutant. Furthermore, mapping the dwf7-1 mutation to the Arabidopsis genome by using simple sequence length polymorphisms (SSLPs; Bell and Ecker (1994) Genomics 19:137–144) confirmed that dwf7 maps to a location different from previously isolated dwarfs. The meiotic recombination ratio between dwf7 and the SSLP marker nga172 on chromosome 3 was scored as 0/86, indicating tight linkage of dwf7 to nga172. According to a recent recombinant inbred map of Arabidopsis, nga172 is located 2.2 centimorgans from the top of chromosome 3.

A second allele of dwf7 was identified among 43 dwarf mutants isolated by screening >50,000 M2 seeds of an EMS mutant population. Similar to dwf7-1, the new allele was biochemically complemented by early BR biosynthetic intermediates, including 22 α-hydroxycampesterol (22-OHCR) and cathasterone, and mapped near nga172. Sequencing revealed a premature stop codon in exon 1 (see below).

EXAMPLE 2

Morphological Analysis of dwf7-1 dwf7 displays many of the characteristics of other BR dwarfs. The characteristic dwarf phenotype, such as short robust stems, reduced fertility, and dark-green, round, and curled leaves are found in the plants. Compared with 1-month-old wild-type plants, dwf7-1 plants grown for 5 weeks in the light possess short robust inflorescences, dark-green, round leaves, reduced fertility, and short pedicels and siliques. The wild-type generally terminates flowering before 7 weeks of age; however, dwf7-1 continues to produce flowers at this age. At 7 weeks of age, wild-type plants had ceased growing, whereas dwf7-1 plants continued to grow, indicating a prolonged life span.

Additional morphological defects of 5-week-old light-grown plants are summarized in Table 1. Most noticeably, the height of dwf7-1 plants is strikingly reduced and is only 14% that of wild-type height. The leaf blade width of dwf7-1 mutants is similar to that of wild-type plants; however, the length is greatly reduced (1.8 cm) as compared with that of the wild type (3 cm), resulting in the round shape of dwf7-1 leaves. The overall morphology of dwf7-2 was similar to dwf7-1 except that it was slightly shorter and more sterile.

TABLE 1

Morphometric Analysis of Wild-Type and dwf7-1Plants at 5 Weeks of Age

| Measurement (n = 15) | Wild Type | dwf7-1 |
|---|---|---|
| Inflorescence | | |
| Height (cm) | 31.6 ± 0.9 | 4.5 ± 0.4 |
| Number of inflorescences | 3.9 ± 0.6 | 4.3 ± 0.5 |
| Reproductive organs | | |
| Number of reproductive organs | 130.2 ± 12.9 | 89.3 ± 20.9 |
| Length of siliques (mm) | 14.8 ± 1.2 | 3.9 ± 0.8 |
| Number of seeds[a] | 49.7 ± 5.1 | 12.4 ± 2.4 |
| Leaf | | |
| Number of resette leaves | 9.1 ± 1.2 | 10.3 ± 1.9 |
| Leaf blade width (cm)[b] | 1.4 ± 0.1 | 1.4 ± 0.3 |
| Leaf blade length (cm)[b] | 3.0 ± 0.3 | 1.8 ± 0.3 |
| Weight | | |
| Fresh weight (g) | 1.50 ± 0.19 | 0.51 ± 0.10 |
| Dry weight (mg) | 215 ± 29 | 53 ± 11 |
| Fresh weight/dry weight | 7.0 ± 0.3 | 9.7 ± 0.6 |

[a]The number of sees per silique was determined after plant senescence.
[b]The second pair of rosette leaves.

Because null mutations in the BR pathway result in a dwarf phenotype, as well as defects in skotomorphogenesis, we compared the dwf7-1 mutant with other BR dwarfs for growth in the dark. Hypocotyl lengths from the longest to the shortest were 18±1.6 (wild-type; units in millimeters±SE; n=15), 6.3±0.29 (dwf7-1), 4.1±0.03 (det2/dwf6), 1.26±0.09 (dwf4), 1.24±0.08 (cpd/dwf3), and 1.18±0.08 (bri1/dwf2). These data indicate that dwf7-1 displays a less severe phenotype (35% that of wild-type hypocotyl length) than do other BR dwarfs (e.g., 7% of wild type in dwf4; Choe et al. (1998) Plant Cell 10:231–243). Furthermore, dwf7-1 frequently displayed closed cotyledons and hooks similar to those of the wild type, whereas severe dwarfs, including bri1/dwf2, cpd/dwf3, and dwf4, showed expanded cotyledons and open hooks.

Figure 2:
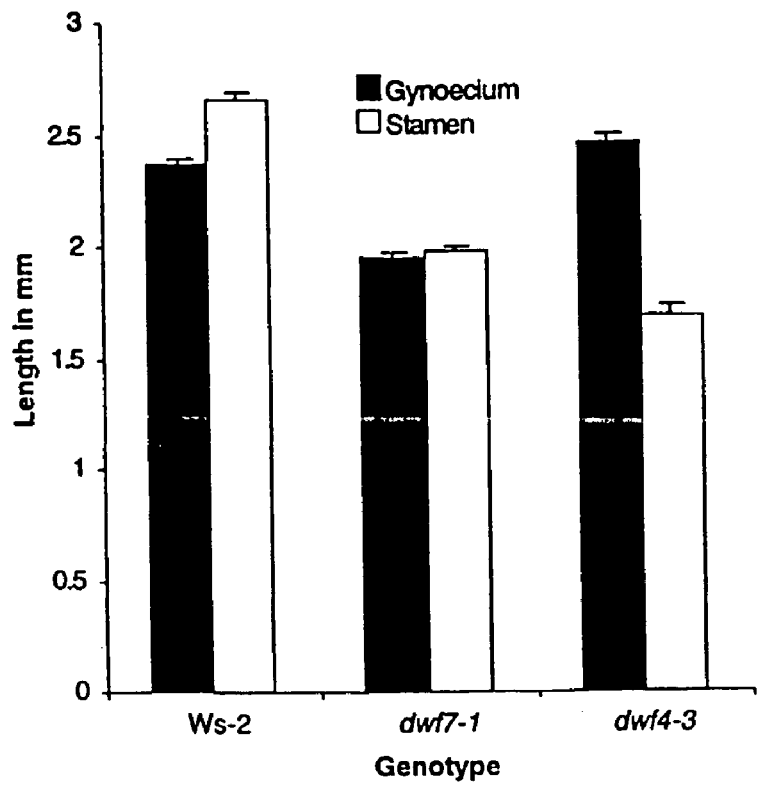
FIG. 2 is a bar graph of measurements of gynoecia and stamens of wild-type, (ecotype Wassilewskija-2 [Ws-2]), dwf7-1, and dwf4-3 plants. The dwf7-1 plant displays a concomitant reduction in the length of gynoecia and stamens, whereas dwf4-3 displays a greater reduction in stamen length. Each data point represents the average length for five flowers. Standard errors are shown at each data point. Solid bars indicate the gynoecium and white bars denote the stamen.

Unlike severe dwarfs, such as dwf4 and cpd, dwf7-1 mutants are not mechanically sterile. However, the average number of seeds in a silique is reduced in dwf7-1 (n=12) compared with that of the wild-type for reasons yet to be identified (n=49) (Table 1). Scanning electron microscopy demonstrated a relationship between fertility and floral structure. In the wild type, the length of stamens was greater than or similar to that of the gynoecium (quantified in FIG. 2), facilitating dehiscence of pollen on the stigmatic surface. The fertile dwf7-1 flower had a concomitant reduction in the size of the gynoecium and the stamen. Although dwf7-1 flowers (FIG. 2) possess stamens and gynoecia that are shorter than those in the wild type, the fertility of dwf7-1 flowers is possible through the concomitant reduction in the length of both organs. In contrast, only stamen elongation was affected more severely in dwf4-3 flowers (FIG. 2). Because sterile dwf4-3 flowers have shorter filaments than the gynoecium, pollen dehiscence on the stigmatic surface is prevented. The short stamen length in dwf4 is likely to cause dehiscence of pollen on the ovary wall rather than on the stigmatic surface. In fact, when dwf4 pollen is transferred to either wild-type or dwf7-1 stigmas, viable seeds are made.

The common denominator for the various phenotypes found in dwf7-1 mutants is a reduction in longitudinal growth, which could be due to either a reduced number of cells or a failure in cell elongation. Observations made with other BR dwarf mutants suggest that the number of cells is comparable in the wild type and mutants (Kauschmann et al. (1996) Plant J. 9:701–713; Nomura et al. (1997) Plant Physiol. 113:31–37; Azpiroz et al. (1998) Plant Cell 10:219–230). The length of cells in the epidermis, cortex, and xylem of dwf7-1 was greatly reduced (<30% of wild type). This reduced cell size was converted to the length of the wild type in response to daily application of $10^{-7}$ M BL for 1 week. Thus, the reduced organ length in dwf7-1 also is due to a failure of cell elongation.

The organization of vascular bundles in wild-type and dwf7-1 mutants was also examined. Wild-type inflorescences possessed eight vascular bundles. However, the number of vascular bundles was reduced to six in dwf7-1. Furthermore, the spacing between the vascular bundles in dwf7-1 was irregular. In the wild type, interfascicular parenchyma cells alternated regularly with vascular bundles; however, cross-sections of dwf7-1 showed that two vascular bundles were joined without being separated by parenchyma cells. Within a single vascular bundle, the size and number of xylem cells in dwf7-1 plants generally were reduced, whereas the number of phloem cells was similar to or even greater than that in the wild-type. This characteristic abnormality of vascular bundle organization has been observed consistently in other BR dwarfs (Szekeres et al. (1996) Cell 85:171–182).

EXAMPLE 3

Biochemical Complementation of dwf7-1 with BL

Figure 3:
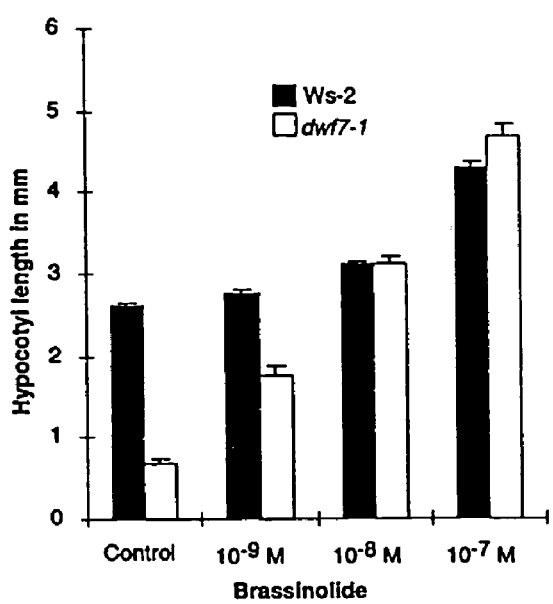
FIG. 3 compares the response of light-grown wild-type and dwf7-1 hypocotyls to different concentrations of BL. Black bars indicate results using the Wassilewskija-2 (Ws-2) wild type and white bars dwf7-1 plants. The dwf7-1 plant responds to $10^{-9}$ M BL and is completely rescued by $10^{-8}$ M BL. Error bars indicate ±SE.

FIG. 3 demonstrates that dwf7-1 seedlings grown in BL-supplemented liquid media were remarkably sensitive to BL. Growth in 1 nM BL induced significant elongation of dwf7-1 hypocotyls (160% increase), whereas the wild-type increase was marginal (5%). Treatment with 10 and 100 nM BL completely rescued dwf7-1 hypocotyls to wild-type length. The strongest response of the wild type to BL was obtained at 100 nM (FIG. 3). Higher concentrations of BL (1 μM) caused a stressed morphology, including inhibition of root growth and swollen, twisted, and fragile hypocotyls in both dwf7-1 and wild-type plants. After BL treatment of dwf7-1, cells in the treated region of the stem were similar in length to wild-type cells.

The overall morphology of plants is dependent on three factors: cell size, shape, and number (Cosgrove (1997) Plant Cell 9:1031–1041). Various signals modulate these factors. Environmental signals, such as water, temperature, and light, are transduced to invoke internal hormone signals, including auxins, gibberellins, and BRs. These signals then trigger the cell elongation process, including but not limited to cell wall loosening by xyloglucan endotransglycosylases and expansins. Thus, a block in any of the signal transduction cascades from the environmental signals to the cell elongation process could result in dwarfism. Mutants resistant to or deficient in classic hormones, such as auxin (e.g., auxin resistant2 [axr2]; Timpte (1992) Genetics 138:1239–1249) and gibberellin ([ga1 to ga5 and gai]; Koornneef and van der Veen (1980) Theor. Appl. Genet. 58:257-263; Koornneef et al. (1985) Physiol. Plant. 65:33–39), often result in dwarfism. Thus, we first tested whether dwf7 is either rescued by or resistant to exogenous application of these hormones. Three-week-old dwf7-1 plants sprayed with 0.1 mM GA$_3$ responded, as did the wild-type (<10% increase of inflorescence height); however, GA$_3$ did not rescue the dwf7-1 phenotype. In addition, dwf7-1 roots grown on indole acetic acid-supplemented agar media (0.1 μM) displayed stunted morphology similar to that of the wild-type, suggesting that dwf7-1 is not resistant to the exogenous application of auxin. The reduction of hypocotyl length in dwf7-1 was rescued by the application of BL (FIG. 3). Both wild-type and dwf7-1 plants responded to BL, but dwf7-1 plants were hypersensitive. The length of dwf7-1 hypocotyls was increased 160% in response to 1 nM BL as compared with the untreated control, whereas the wild-type responded marginally (5%). In addition, application of BRs to 3-week-old dwf7-1 plants induced the growth of many different organs, including stems, leaves, siliques, petioles, and pedicels, suggesting that the major defect in dwf7-1 is a deficiency of BL.

Apart from a reduction in cell elongation, a deficiency of endogenous BRs resulted in altered organization of vascular tissue in the inflorescence. Szekeres et al. (1996) Cell 85:171–182 showed that the number of xylem cells in cpd was decreased as compared with the wild-type, whereas the number of phloem cells was increased. The authors reasoned that this could be due to unequal division of cambial cells. Furthermore, previous studies on the effects of BRs on vascular development indicated that BRs play a role in tracheary element formation (Clouse and Zurek (1991) Molecular analysis of brassinolide action in plant growth and development. In Brassinosteroids: Chemistry, Bioactivity and Applications, H. G. Cutler, T. Yokota, and G. Adam, eds (Washington D.C.: American Chemical Society), pp. 122–140; Iwasaki and Shibaoka (1991) Plant Cell. Physiol. 32:1007–101). Because BRs also have been found in the cambial region of pine, indicative of an important role in this tissue (Kim et al. (1990) Plant Physiol. 94:1709–1713), we hypothesize that the deficiency of BRs in dwarf mutants caused changes in cell fate in vascular cambial cells through yet unknown mechanisms.

Auxins also are known to be a major factor affecting differentiation of the vascular system (Aloni (1987) Annu. Rev. Plant Physiol. 38:179–204). Lincoln et al. (1990) Plant Cell 2:1071–1080 showed that stem cross-sections of axr1 displayed altered development of the vascular system. The vascular bundles in axr1 mutants are located peripherally and are not as regularly spaced as compared with those in wild-type plants (Lincoln et al. (1990) Plant Cell 2:1071–1080). Furthermore, as opposed to the reduced number of vascular bundles in dwf7-1 (five to seven), axr1 plants possess a greater number of bundles (eight to nine) as compared with the wild type (six to eight). Thus, it seems that auxins and BRs play opposing roles in determining the number of vascular bundles. Two other assays in which auxin and BR interactions have been demonstrated are the rice lamina bending assay and hypocotyl hook opening bioassay. Results from these assays include the fact that the degree of effect caused by the combined application of auxin and BR was greater than was the sum of the effect of each, indicative of a synergistic effect of the two hormones (Yopp et al. (1981) Physiol. Plant. 53:445–452; Takeno and Pharis (1982) Plant Cell Physiol. 23:1275–1281 reviewed in Mandava (1988) Annu. Rev. Plant Physiol. Plant Mol. Biol. 39:23–52). However, the details of the mechanisms for interactive and independent action remain to be elucidated.

It needs to be pointed out that hypocotyl growth in darkness is accomplished through both GA- and BR-dependent cell elongation processes. One piece of evidence for dependence on both GA and BR is that dwf7-1 hypocotyls elongated fivefold in response to darkness as compared with light-grown hypocotyls, although they are still shorter than those of the wild-type. Because BL levels are not detectable in dwf7-1 plants (Table 2), growth of dwf7-1 in the dark could be accomplished mostly by GA-dependent cell elongation processes. Peng and Harberd (1997) Plant Physiol. 113:1051–1058 and Azpiroz et al. (1998) Plant Cell 10:219–230 found that both gai and dwf4, respectively, partially suppressed the stem elongation phenotype of a light receptor mutant, hy, suggesting that hypocotyl elongation in the absence of light inhibition requires independent growth contributed by both GA and BRs.

EXAMPLE 4

Identification of the BR Biosynthetic Defect in dwf7-1

Biochemical complementation of dwf7-1 following application of BL suggested that dwf7-1 is likely to be defective in BR biosynthesis. To pinpoint the defective step in the BR biosynthetic pathway, dwf7-1 mutants were treated with BR biosynthetic intermediates. Due to undetectable bioactivity of some early intermediates (CR to 6-oxocampestanol) in bioassays (Fujioka et al. 1995; Choe et al. (1998) Plant Cell 10:231–243), these were not used. Instead, three biologically active compounds were chosen, 22-OHCR, 6-deoxoCT, and BL, for these feeding tests (see FIG. 1). Because the 22α-hydroxylation reaction is reported to be mediated by DWF4 (Choe et al. (1998) Plant Cell 10:231–243), biochemical complementation of dwf mutants other than dwf4 by 22-OHCR places the defective step upstream of CR.

Complementing compounds induced growth of internodes and strongly increased pedicel length. The dwf7-1 pedicels treated with 22-OHCR and BL showed growth greater than or equal to that of the wild-type. Measurements of pedicel length shown in FIG. 4 demonstrated that the three compounds tested, 22-OHCR, 6-deoxoCT, and BL, all increased dwf7-1 pedicel length >200% as compared with the control, suggesting that the defective step in BR biosynthesis is located at or before the CR biosynthetic step. Similarly, 3-week-old inflorescences of dwf7-2 were tested with 22-OHCR, 6-deoxoCT, teasterone, and BL. All four compounds induced significant elongation of pedicels and internodes, indicating that dwf7-1 and dwf7-2 share the same biosynthetic defect.

Figure 4:
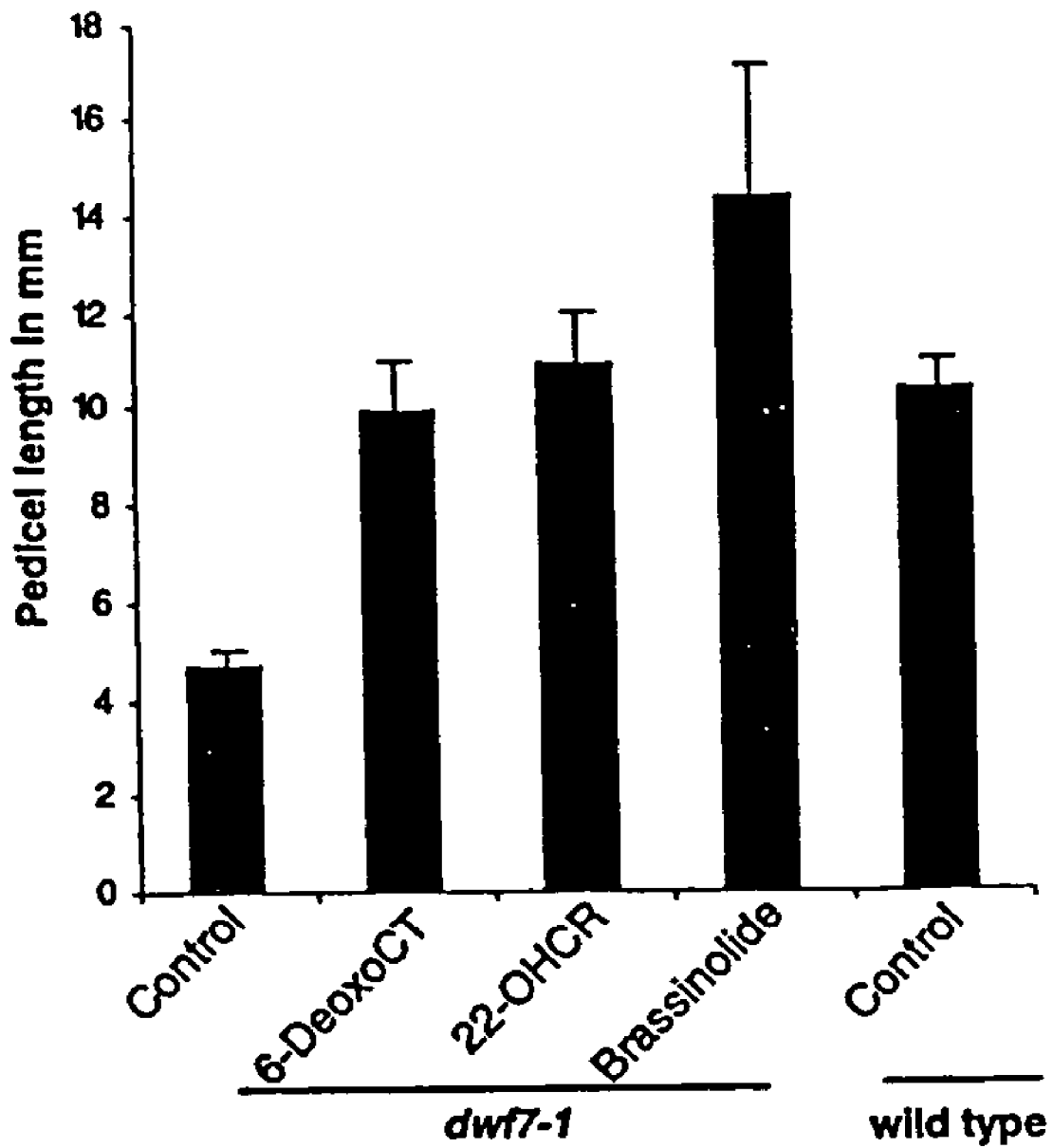
FIG. 4 is a bar graph comparing wild-type and dwf7-1 inflorescences treated with BR intermediates. The lengths of pedicels treated with water, 6-deoxoCT, 22-OHCR, and BL were measured to the nearest millimeter (n>15). The pedicels elongated greater than twofold in response to all the BRs tested, suggesting that the biosynthetic defect in dwf7-1 resides before the production of CR. Error bars indicate ±SE.

As shown in Table 2, more definitive results indicating a specific defect in BR biosynthesis have been obtained from gas chromatography-selective ion monitoring (GC-SIM) analysis of endogenous BRs and sterols in dwf7-1 plants. The endogenous levels of sterols, such as 24-MC, CR, and campestanol (CN), in wild-type plants, were 3800, 32,900, and 1140 ng/g fresh weight, respectively. However, the levels of all three sterols in dwf7-1 mutants were extremely diminished at 3.1, 1.1, and 1.4% of the wild-type, respectively, suggesting that the biosynthetic block is located before 24-MC. These data are consistent with the results of intermediate feeding studies (FIG. 4).

TABLE 2

Quantification of Endogenous BRs from Wild Type and dwf7-1 by Using GC-SIM

| BRs | Wild Type[a] | dwf7-1 |
| --- | --- | --- |
| 34-MC | 3,800 | 118 |
| CR | 32,900 | 379 |
| CN | 1,140 | 16 |
| 6-Deoxoteasterone | 0.05 | NA[b] |
| 6-Deoxotyphasterol | 2.3 | NA |
| 6-Deoxocastasterone | 4.0 | ND[c] |
| Typhasterol | 0.27 | ND |
| CS | 0.28 | 0.13 |
| BL | 0.2 | ND |

[a]The unit of measurement is nanograms per gram fresh weight.
[b]NA, not analyzed.
[c]ND, not detected. The endogenous amount of the BR is less than the detection limit (~0.05 ng/g fresh weight).

Figure 5:
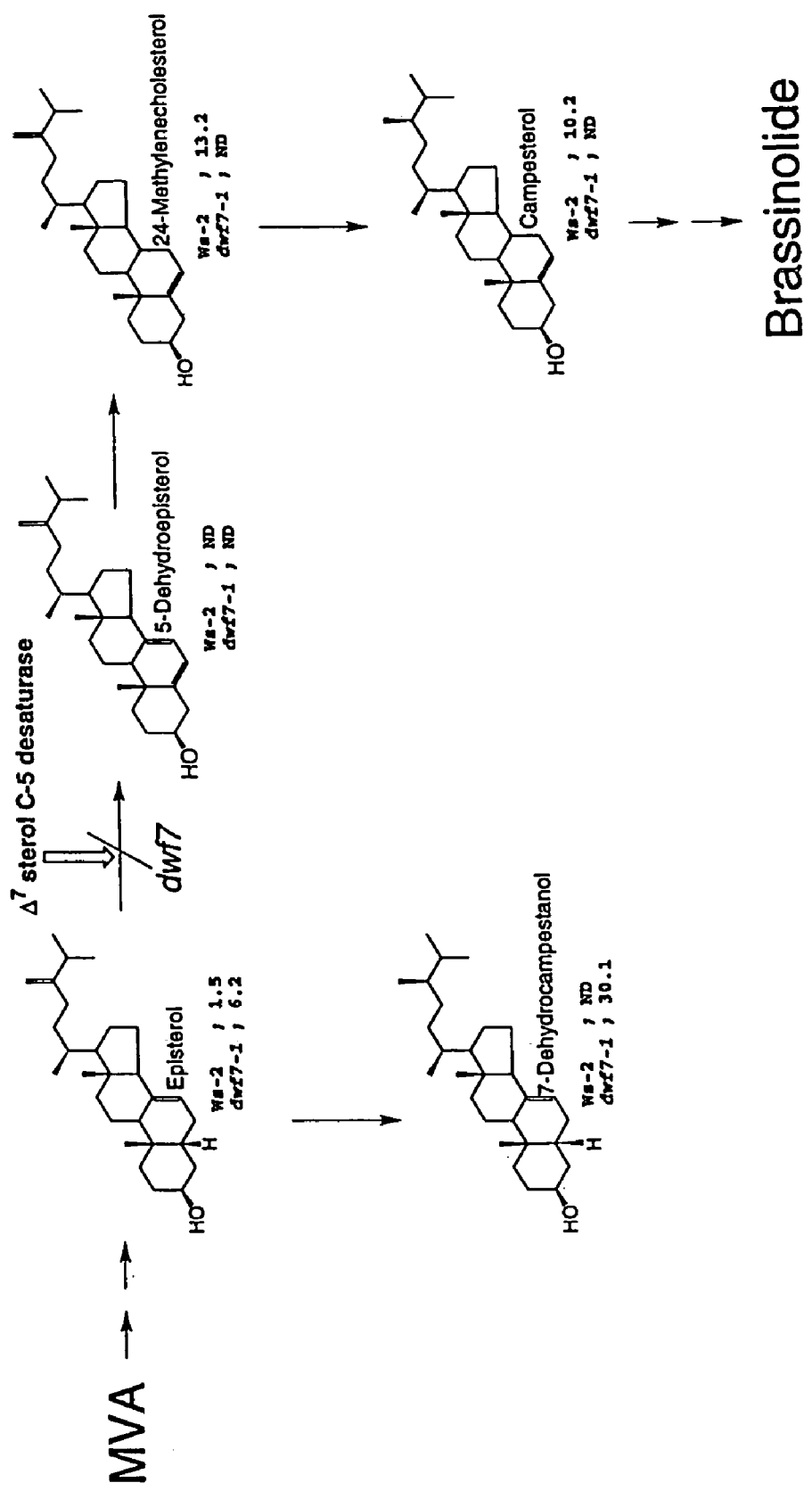
FIG. 5 shows GC-MS analysis of wild-type and dwf7-1 seedlings fed with $^{13}$C-MVA in the presence of compactin, an inhibitor of MVA biosynthesis. Accumulation of episterol with a simultaneous decrease of downstream intermediates, including 24-MC and CR, predicts that the C-5 desaturation step is blocked in dwf7-1 plants. The units are in micrograms per 5 g fresh weight of tissue. The designation ND (not detected) means that the quantity is lower than the detection limit. Ws-2 is the Wassilewskija-2 wild type.

Further biochemical feeding studies with $^{13}$C-labeled mevalonic acid (MVA) and compactin, a MVA biosynthetic inhibitor, were performed to identify the specific sterol biosynthetic step defective in dwf7-1 plants. In a preliminary experiment, the effects of compactin and MVA on the growth of Arabidopsis seedlings in liquid media were investigated. The growth of wild-type Arabidopsis seedlings was almost completely inhibited in the presence of 10 µM compactin. The inhibition, however, was restored to the level of controls by the simultaneous application of 4.5 mM of MVA. Therefore, 4.5 mM $^{13}$C-MVA and 10 µM compactin were added to Arabidopsis seedling cultures in the metabolic feeding studies. After 11 days in culture, sterols were extracted and purified by silica and octadecylsilane (ODS) cartridge columns and ODS-HPLC. Purified samples were derivatized and analyzed by gas chromatography-mass spectrometry (GC-MS). As shown in FIG. 5, $^{13}$C-MVA was converted to $^{13}C_5$-episterol and subsequent sterols, such as $^{13}C_5$-24-MC and $^{13}C_5$-CR in the wild-type. However, the $^{13}C_5$-5-dehydroepisterol and downstream compounds were not detected in dwf7-1 mutants, whereas the precursor $^{13}C_5$-episterol accumulated fourfold as compared with the wild-type. In addition, an uncommon sterol, $^{13}C_5$-7-dehydrocampestanol (24-epifungisterol), greatly accumulated (FIG. 5). Two lines of evidence-a failure to convert episterol to subsequent sterols, such as 24-MC and CR, and accumulation of 7-dehydrocampestanol in dwf7-1-suggest that the defective step in dwf7-1 is the C-5 desaturation stop.

A defect either in a biosynthetic enzyme or a factor modulating an enzymatic activity could lead to deficiency of endogenous BRs. To place dwf7 at a specific step in the proposed BR biosynthetic pathway, we first chose to perform feeding studies with BR biosynthetic intermediates. Rescue of dwf7-1 by exogenous application of 22-OHCR suggests that the biosynthetic defect likely resides before the production of CR. Consistent with the results from feeding studies, the endogenous levels of 24-MC, CR, and CN were extremely reduced in dwf7-1 (Table 2). These data indicate that the biosynthetic defect is before 24-MC; dwf7-1 contains only 3% of 24-MC as compared with the wild type. When the phenotypes of dwf7-1 are compared with the downstream biosynthetic mutant dwf4 and the BR-insensitive bri1 (dwf2) mutant (Clouse et al. (1996) Plant Physiol. 111:671–678), it is obvious that dwf7-1 displays a weaker phenotype despite being a presumptive null mutation. This suggests that there could be an alternative sterol and BR biosynthetic pathway or that there are duplicate genes at individual steps. Providing evidence for the duplicate gene hypothesis, we recently cloned a homolog of the DWF7/STE1 gene (named HOMOLOG OFDWF7, HDF7), shown in FIGS. 10 and 11 (GenBank Accession No. AAF32466). HDF7 is 80% identical in amino acid sequence with STE1. Similarly, Fujioka et al. 1997 reported that the endogenous level of CN in det2, which is defective in a step between CR and CN, is ~10% that of the wild-type amount. The authors hypothesized that the 10% leakage through the defective step in det2 mutants, even in a null allele, could be associated with a second copy of DET2 that lightly hybridizes in DNA gel blot analyses.

Placing dwf7 at a single sterol biosynthetic step was accomplished through feeding studies with $^{13}$C-MVA and compactin. A greater than fourfold accumulation of episterol accompanying the absence of downstream intermediates in dwf7-1 indicates that the $\Delta^7$ sterol C-5 desaturase step is blocked in dwf7. In addition, the feeding studies identified an accumulation of 7-dehydrocampestanol, which is an uncommon sterol in plants (FIG. 5). Accumulation of this compound only in dwf7-1 suggests that sterol biosynthesis in dwf7-1 could proceed to a C-24 reduction step, skipping C-5 desaturation as well as the next immediate C-7 reduction. The C-24 reductase seems to convert episterol independently of the immediate upstream enzyme. The absence of a detectable amount of C-7-reduced compounds in dwf7-1 suggests that the enzymatic step is highly dependent on the C-5 desaturation reaction. This confirms the sequence of reactions originally proposed by Taton and Rahier (1991) Biochem. Biophys. Res. Commun. 181:465–473, Taton and Rahier (1996) Arch. Biochem. Biophys. 325:279–288.

EXAMPLE 5

Molecular Characterization of dwf7

An EMS-induced mutant (ste1-1) of STE1 encoding a $\Delta^7$ sterol C-5 desaturase did not possess a dwarf phenotype (Gachotte et al. (1995) Plant J. 8:407–416). However, because it is likely that ste1-1 is a leaky allele, it was hypothesized that dwf7-1 might be a strong or null allele. The genomic DNA of the STE1 gene was sequenced and two introns and three exons identified by comparing them with the published STE1 cDNA sequence. The organization of the STE1 gene is represented schematically in FIG. 6. Sequencing the STE1 locus in the dwf7 alleles revealed mutations. The mutations found in dwf7-1 and dwf7-2 were located in the third and the first exons, respectively. Both of the dwf7 alleles contained a base change from a guanine to an adenine, converting tryptophan (TGG) to a stop codon (TAG in dwf7-1 and TGA in dwf7-2).

In addition to creating a stop codon, the mutation in dwf7-1 eliminated a HaeIII restriction enzyme recognition site (GGCC to AGCC). Taking advantage of this restriction enzyme site change, we tested the linkage of this mutation to the dwf7-1 phenotype. DNAs isolated from 17 different dwarf plants from a segregating $F_2$ population were subjected to polymerase chain reaction (PCR) analysis by using S5D_3F and S5D_1R primers (underlines were used to distinguish forward or reverse primers from the gene acronym S5D), and the PCR products were digested with HaeIII. Agarose gel electrophoresis definitively showed that none of the PCR products from 17 mutant templates was restricted, whereas products from wild-type templates were all restricted at the HaeIII site. These data suggest that the creation of the premature stop codon in exon 3 is the cause of the dwf7-1-conferred phenotype.

To better understand the importance of these nonsense mutations, we analyzed the sequence of STE1 in relation to other C-5 desaturase proteins isolated from fungi. The STE1 protein is composed of 281 predicted amino acids with a theoretical pI of 6.39 and molecular mass of 33 kD. Whereas yeast ERG3 (38% identical; Arthington et al. (1991) Gene 107:173–174; GenBank accession number M62623) is predicted to contain four transmembrane domains, STE1 possesses three putative transmembrane domains. The overall amino acid sequence identities of STE1 with C-5 desaturases from fission yeast (GenBank accession number AB004539) and Candida glabrata (Geber et al. (1995) Antimicrob. Agents Chemother. 39:2708–2717; GenBank accession number L40390) were 37 and 33%, respectively (gap creation weight of 4; gap extension weight of 1). In addition, multiple sequence alignment of STE1 with the three yeast sequences, shown in FIG. 7, revealed that the transmembrane domains and histidine clusters, which were first reported by Gachotte et al. (1996) Plant J. 9:391–398, are well conserved between the proteins. The three characteristic histidine boxes flank the last transmembrane domain. The nonsense mutations are located in the first exon (dwf7-2) and the third exon, immediately before the third histidine box (dwf7-1), indicating that at least one histidine domain is deleted in each of the dwf7 mutants as a result of the premature stop codons.

The $\Delta^7$ sterol C-5 desaturase-mediated reaction is common to both photosynthetic and nonphotosynthetic organisms. Many genes encoding a C-5 desaturase have been cloned from fungi. First, Arthington et al. (1991) Gene 107:173–174 cloned the ERG3 gene from *Saccharomyces cerevisiae*. The authors found that viable erg3 mutants, which normally accumulate $\Delta^7$ sterols, were restored to wild-type phenotype when transformed with a wild-type genomic clone of the $\Delta^7$ sterol C-5 desaturase gene. Taguchi et al. (1994) Microbiology 140:353–359 showed that the yeast mutant syr1 displays dual phenotypes, resistance to the phytotoxin syringomycin and susceptibility to higher concentrations of $Ca^{2+}$, presumably due to altered membranes. Sequencing the ERG3 locus in the syr1 mutant revealed that syr1 is an allele of ERG3. Furthermore, Geber et al. (1995) Antimicrob. Agents Chemother. 39:2708–2717 cloned both ERG3 and ERG11 (14α-sterol-demethylase) from *C. glabrata*. The authors found that lethal erg11 mutations can be suppressed by an additional mutation in erg3. They reasoned that formation of toxic 3β,6α-diol sterols in erg11 mutants is prevented due to the defect in C-5 desaturation in erg11 erg3 double mutants.

Figure 7:
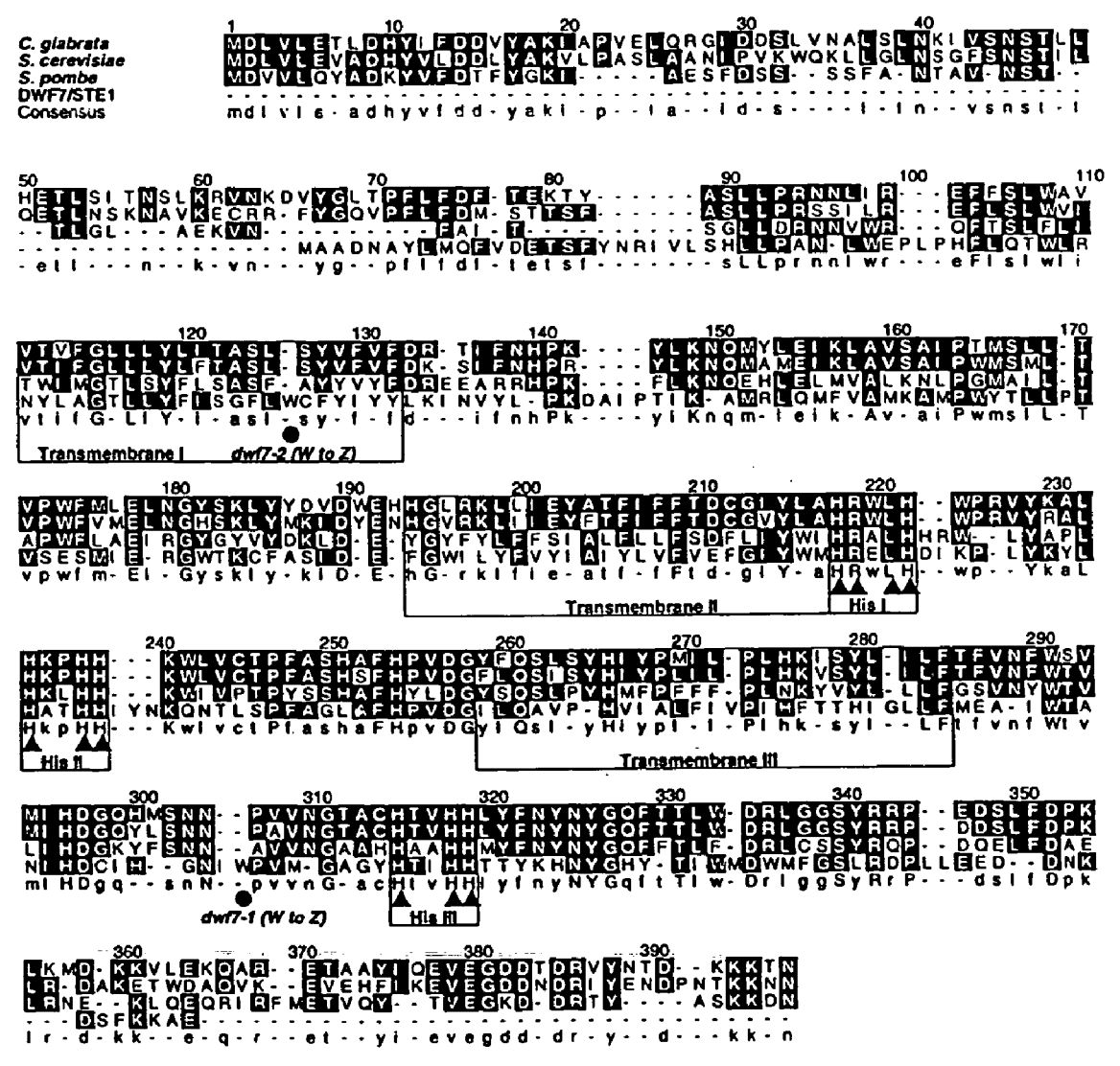

In plants, Gachotte et al. (1995) Plant J. 8:407–416 found that the Arabidopsis ste1-1 mutant, which is deficient in C-5 desaturated sterols, can be partially complemented by the yeast ERG3 gene. Accordingly, the authors hypothesized that ste1-1 possesses a mutation in the sterol C-5 desaturase gene. They isolated the Arabidopsis C-5 desaturase gene through heterologous complementation of a yeast erg3 null mutant with an Arabidopsis cDNA library (Gachotte et al. (1996) Plant J. 9:391-398). Finally, the partial human cDNA for the C-5 desaturase has been identified by Matsushima et al. (1996) Cell Genet. 74:252–254. Alignment of the sequences of these enzymes revealed that C-5 desaturases from different organisms are highly conserved in overall sequence as well as in specific domains. The overall amino acid sequence identity and similarity among STE1 and ERG3 and the human ortholog is 38% (50%) and 35% (47%), respectively (similarity within parentheses). As indicated in FIG. 6 and FIG. 7, key domains including the transmembrane domains and the histidine clusters are well conserved between all the C-5 desaturases.

Closely spaced histidine residues, $HX_3H$ in helices, serve as typical metal binding motifs in many proteins (Regan (1993) Annu. Rev. Biophys. Biomol. Struct. 22:257–281). Shanklin et al. (1994) Biochemistry 33:12787–12794 showed that three membrane-associated bacterial enzymes, fatty acid desaturase, alkane hydroxylase, and xylene monooxygenase, possess eight histidine residues that are conserved in three regions dispersed in these enzymes, $HX_{(3-4)}H$, $HX_{(2-3)}HH$, and $HX_{(2-3)}HH$ (where X stands for any amino acid). DNA constructs containing site-directed mutations at any of these eight histidine residues of the rat $\Delta^9$ desaturase failed to complement the yeast mutant ole1, which is defective in the same enzymatic step, suggesting that the individual histidine residues are essential for the function of the enzyme. On the basis of these observations, Shanklin et al. (1994) Biochemistry 33:12787–12794 hypothesized that the histidine clusters conserved in these enzymes constitute new structural domains of diiron binding centers (Shanklin et al. (1994) Biochemistry 33:12787–12794). Gachotte et al. (1996) Plant J. 9:391–398 first recognized the conserved histidine clusters in STE1 and yeast proteins. We confirmed that the motifs are highly conserved in STE1 and the yeast ERG3 enzymes with the same context of $HX_3H$, $HX_2HH$, and $HX_2HH$ (FIG. 7), revealing the presence of a putative iron binding motif in $\Delta^7$ sterol C-5 desaturases.

More direct evidence of metal ion involvement in $\Delta^7$ sterol C-5 desaturase function was obtained by Taton and Rahier (1996) Arch. Biochem. Biophys. 325:279–288. These authors discovered that the enzyme prepared from maize microsomes is inhibited by cyanide, whereas it is insensitive to carbon monoxide, indicative of the involvement of a metal ion, presumably an iron, for the proper function of the enzyme. Furthermore, we noticed that the typical histidine moiety also was conserved in a different group of oxidases such as RANP-1 (Uwabe et al. (1997) Neuroscience 80:501–509), C-4 methyl sterol oxidase (Li and Kaplan (1996) J. Biol. Chem. 271:16927–16933), and aldehyde decarbonylase (Aarts et al. (1995) Plant Cell 7:2115–2127). Occurrence of these histidine boxes in a wide variety of oxidases indicates that this domain plays a common and essential role in the function of membrane oxidases. Therefore, it is likely that the mutations in dwf7-1 and dwf7-2 would be deleterious to protein function. The premature stop codon in dwf7-2 would eliminate all important known domains, whereas the third histidine box and several amino acid residues that are 100% conserved in the C terminus of the protein are eliminated in dwf7-1. Intriguingly, the location of the mutations in dwf7-1 and dwf 7-2 seems to be related to the phenotypic severity of the mutant alleles. dwf7-2, which contains an earlier stop codon, was shorter in height and less fertile than dwf7-1. A more precise comparison between the two alleles is not possible because the EMS allele, dwf7-2, has not been outcrossed to remove any background mutations that might have increased the severity of the phenotype of dwf7-2. Despite the differences in severity, both dwf7 alleles are likely complete loss-of-function alleles. The resulting nonfunctional enzyme causes a block in sterol biosynthesis. This shortage of substrate sterols in dwf7-1 and dwf7-2 leads to a deficiency of endogenous BRs and causes the characteristic dwarfism in dwf7 plants.

Thus, novel dwf7 mutants, as well as methods of using the same, are disclosed. Although preferred embodiments of the subject invention have been described in some detail, it is understood that obvious variations can be made without departing from the spirit and the scope of the invention as defined by the appended claims.

We claim:

1. An isolated polynucleotide comprising a nucleic acid sequence encoding a polypeptide having the amino acid sequence set forth in SEQ ID NO:23.

2. A recombinant vector comprising the isolated polynucleotide of claim 1.

3. The vector of claim 2, wherein said polynucleotide is operably linked to a control element.

4. An isolated cell comprising an exogenous polynucleotide, said exogenous polynucleotide comprising a nucleic acid sequence encoding a polypeptide having the amino acid sequence set forth in SEQ ID NO:23.

5. A plant comprising an exogenous polynucleotide, said exogenous polynucleotide comprising a control element operably linked to a nucleic acid sequence encoding a polypeptide having the amino acid sequence set forth in SEQ ID NO:23.

* * * * *

UNITED STATES PATENT AND TRADEMARK OFFICE
CERTIFICATE OF CORRECTION

| | | |
|---|---|---|
| PATENT NO. | : 7,183,459 B2 | Page 1 of 1 |
| APPLICATION NO. | : 10/736318 | |
| DATED | : February 27, 2007 | |
| INVENTOR(S) | : Sunghwa Choe and Kenneth A. Feldmann | |

It is certified that error appears in the above-identified patent and that said Letters Patent is hereby corrected as shown below:

Column 1, line 2, please insert

--STATEMENT AS TO FEDERALLY FUNDED RESEARCH

This invention was made with government support under IBN9604439 awarded by the National Science Foundation. The government has certain rights in the invention.--

Signed and Sealed this

Second Day of September, 2008

JON W. DUDAS
*Director of the United States Patent and Trademark Office*

SEQUENCE LISTING

```
<160> NUMBER OF SEQ ID NOS: 25

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence:
      Primer S5D_FF

<400> SEQUENCE: 1
cagtgtgagt aatttagcat tacta                                      25

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence:
      Primer S5D_LR

<400> SEQUENCE: 2
ggaaagatca tcaaacattt acatgt                                     26

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence:
      Primer S5D_1F

<400> SEQUENCE: 3
gcgcaatctt ctttcgttt                                             19

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:
      Primer S5D_1R

<400> SEQUENCE: 4
tggacaacaa caacacaaga                                            20

<210> SEQ ID NO 5
<211> LENGTH: 22
```

```
<212> TYPE: DNA
<213> ORGANISM: Artificial Sequence
<220> FEATURE:
<223> OTHER INFORMATION: Description of Artificial Sequence:
      Primer S5D_2F

<400> SEQUENCE: 5
gatgcacaga gagcttcatg ac                                              22

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence:
      Primer S5D_2R

<400> SEQUENCE: 6
ccggcaaatg gagagagtgt at                                              22

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence:
      Primer S5D_3F

<400> SEQUENCE: 7
cacccatcat atctacaaca a                                               21

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence:
      Primer S5D_4F

<400> SEQUENCE: 8
catcttttgc cggcgaatct at                                              22

<210> SEQ ID NO 9
<211> LENGTH: 32
<212> TYPE: DNA
<213> ORGANISM: Artificial Sequence
<220> FEATURE:
<223> OTHER INFORMATION: Description of Artificial Sequence:
      Primer D7-5-1

<400> SEQUENCE: 9
gtagaagcac cagaggaaac cggagatgaa gt                                   32

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence:
      Primer D7-5-2

<400> SEQUENCE: 10
aagtatagta gggttccggc gaggta                                          26

<210> SEQ ID NO 11
<211> LENGTH: 26
<212> TYPE: DNA
```

```
<213> ORGANISM: Artificial Sequence
<220> FEATURE:
<223> OTHER INFORMATION: Description of Artificial Sequence:
      Primer D7-5-3

<400> SEQUENCE: 11
atagattcgc cggcaaaaga tgactc                                      26

<210> SEQ ID NO 12
<211> LENGTH: 32
<212> TYPE: DNA
<213> ORGANISM: Artificial Sequence
<220> FEATURE:
<223> OTHER INFORMATION: Description of Artificial Sequence:
      Primer D7-3-1

<400> SEQUENCE: 12
tgcaggatac catacgatac accacacgac at                               32

<210> SEQ ID NO 13
<211> LENGTH: 35
<212> TYPE: DNA
<213> ORGANISM: Artificial Sequence
<220> FEATURE:
<223> OTHER INFORMATION: Description of Artificial Sequence:
      Primer D7-3-2

<400> SEQUENCE: 13
catacgatac accacacgac atacaagcat aacta                            35

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence:
      Primer D7-3-3

<400> SEQUENCE: 14
atatggatgg attggatgtt tggctctc                                    28

<210> SEQ ID NO 15
<211> LENGTH: 364
<212> TYPE: PRT
<213> ORGANISM: delta-7 sterol C-5 desaturase (Candida glabrata)

<400> SEQUENCE: 15
```

Met Asp Leu Val Leu Glu Thr Leu Asp His Tyr Ile Phe Asp Asp Val
 1               5                  10                  15

Tyr Ala Lys Ile Ala Pro Val Glu Leu Gln Arg Gly Ile Asp Asp Ser
            20                  25                  30

Leu Val Asn Ala Leu Ser Leu Asn Lys Ile Val Ser Asn Ser Thr Leu
        35                  40                  45

Leu His Glu Thr Leu Ser Ile Thr Asn Ser Leu Lys Arg Val Asn Lys
    50                  55                  60

Asp Val Tyr Gly Leu Thr Pro Phe Leu Phe Asp Phe Thr Glu Lys Thr
65                  70                  75                  80

Tyr Ala Ser Leu Leu Pro Arg Asn Asn Leu Ile Arg Glu Phe Phe Ser
                85                  90                  95

Leu Trp Ala Val Val Thr Val Phe Gly Leu Leu Tyr Leu Ile Thr
            100                 105                 110

Ala Ser Leu Ser Tyr Val Phe Val Phe Asp Arg Thr Ile Phe Asn His
        115                 120                 125

```
Pro Lys Tyr Leu Lys Asn Gln Met Tyr Leu Glu Ile Lys Leu Ala Val
    130                 135                 140

Ser Ala Ile Pro Thr Met Ser Leu Leu Thr Val Pro Trp Phe Met Leu
145                 150                 155                 160

Glu Leu Asn Gly Tyr Ser Lys Leu Tyr Tyr Asp Val Asp Trp Glu His
                165                 170                 175

His Gly Leu Arg Lys Leu Leu Ile Glu Tyr Ala Thr Phe Ile Phe Phe
            180                 185                 190

Thr Asp Cys Gly Ile Tyr Leu Ala His Arg Trp Leu His Trp Pro Arg
        195                 200                 205

Val Tyr Lys Ala Leu His Lys Pro His His Lys Trp Leu Val Cys Thr
    210                 215                 220

Pro Phe Ala Ser His Ala Phe His Pro Val Asp Gly Tyr Phe Gln Ser
225                 230                 235                 240

Leu Ser Tyr His Ile Tyr Pro Met Ile Leu Pro Leu His Lys Ile Ser
                245                 250                 255

Tyr Leu Ile Leu Phe Thr Phe Val Asn Phe Trp Ser Val Met Ile His
            260                 265                 270

Asp Gly Gln His Met Ser Asn Asn Pro Val Val Asn Gly Thr Ala Cys
        275                 280                 285

His Thr Val His His Leu Tyr Phe Asn Tyr Asn Tyr Gly Gln Phe Thr
    290                 295                 300

Thr Leu Trp Asp Arg Leu Gly Gly Ser Tyr Arg Arg Pro Glu Asp Ser
305                 310                 315                 320

Leu Phe Asp Pro Lys Leu Lys Met Asp Lys Lys Val Leu Glu Lys Gln
                325                 330                 335

Ala Arg Glu Thr Ala Ala Tyr Ile Gln Glu Val Glu Gly Asp Asp Thr
            340                 345                 350

Asp Arg Val Tyr Asn Thr Asp Lys Lys Lys Thr Asn
        355                 360

<210> SEQ ID NO 16
<211> LENGTH: 365
<212> TYPE: PRT
<213> ORGANISM: delta-7 sterol C-5 desaturase (Saccharomyces cerevisiae)

<400> SEQUENCE: 16

Met Asp Leu Val Leu Glu Val Ala Asp His Tyr Val Leu Asp Asp Leu
1               5                   10                  15

Tyr Ala Lys Val Leu Pro Ala Ser Leu Ala Ala Asn Ile Pro Val Lys
                20                  25                  30

Trp Gln Lys Leu Leu Gly Leu Asn Ser Gly Phe Ser Asn Ser Thr Ile
            35                  40                  45

Leu Gln Glu Thr Leu Asn Ser Lys Asn Ala Val Lys Glu Cys Arg Arg
        50                  55                  60

Phe Tyr Gly Gln Val Pro Phe Leu Phe Asp Met Ser Thr Thr Ser Phe
65                  70                  75                  80

Ala Ser Leu Leu Pro Arg Ser Ser Ile Leu Arg Glu Phe Leu Ser Leu
                85                  90                  95

Trp Val Ile Val Thr Ile Phe Gly Leu Leu Leu Tyr Leu Phe Thr Ala
            100                 105                 110

Ser Leu Ser Tyr Val Phe Val Phe Asp Lys Ser Ile Phe Asn His Pro
        115                 120                 125

Arg Tyr Leu Lys Asn Gln Met Ala Met Glu Ile Lys Leu Ala Val Ser
```

```
                    130                 135                 140
Ala Ile Pro Trp Met Ser Met Leu Thr Val Pro Trp Phe Val Met Glu
145                 150                 155                 160

Leu Asn Gly His Ser Lys Leu Tyr Met Lys Ile Asp Tyr Glu Asn His
                165                 170                 175

Gly Val Arg Lys Leu Ile Ile Glu Tyr Phe Thr Phe Ile Phe Phe Thr
            180                 185                 190

Asp Cys Gly Val Tyr Leu Ala His Arg Trp Leu His Trp Pro Arg Val
        195                 200                 205

Tyr Arg Ala Leu His Lys Pro His His Lys Trp Leu Val Cys Thr Pro
210                 215                 220

Phe Ala Ser His Ser Phe His Pro Val Asp Gly Phe Leu Gln Ser Ile
225                 230                 235                 240

Ser Tyr His Ile Tyr Pro Leu Ile Leu Pro Leu His Lys Val Ser Tyr
                245                 250                 255

Leu Ile Leu Phe Thr Phe Val Asn Phe Trp Thr Val Met Ile His Asp
            260                 265                 270

Gly Gln Tyr Leu Ser Asn Asn Pro Ala Val Asn Gly Thr Ala Cys His
        275                 280                 285

Thr Val His His Leu Tyr Phe Asn Tyr Asn Tyr Gly Gln Phe Thr Thr
    290                 295                 300

Leu Trp Asp Arg Leu Gly Gly Ser Tyr Arg Arg Pro Asp Asp Ser Leu
305                 310                 315                 320

Phe Asp Pro Lys Leu Arg Asp Ala Lys Glu Thr Trp Asp Ala Gln Val
                325                 330                 335

Lys Glu Val Glu His Phe Ile Lys Glu Val Glu Gly Asp Asp Asn Asp
            340                 345                 350

Arg Ile Tyr Glu Asn Asp Pro Asn Thr Lys Lys Asn Asn
        355                 360                 365

<210> SEQ ID NO 17
<211> LENGTH: 329
<212> TYPE: PRT
<213> ORGANISM: delta-7 sterol C-5 desaturase
      (Schizosaccharomyces pombe)

<400> SEQUENCE: 17

Met Asp Val Val Leu Gln Tyr Ala Asp Lys Tyr Val Phe Asp Thr Phe
1               5                   10                  15

Tyr Gly Lys Ile Ala Glu Ser Phe Asp Ser Ser Ser Phe Ala Asn
            20                  25                  30

Thr Ala Val Asn Ser Thr Thr Leu Gly Leu Ala Glu Lys Val Asn Phe
        35                  40                  45

Ala Ile Thr Ser Gly Leu Leu Asp Arg Asn Asn Val Trp Arg Gln Phe
    50                  55                  60

Thr Ser Leu Phe Leu Ile Thr Trp Ile Met Gly Thr Leu Ser Tyr Phe
65                  70                  75                  80

Leu Ser Ala Ser Phe Ala Tyr Tyr Val Tyr Phe Asp Arg Glu Glu Ala
                85                  90                  95

Arg Arg His Pro Lys Phe Leu Lys Asn Gln Glu His Leu Glu Leu Met
            100                 105                 110

Val Ala Leu Lys Asn Leu Pro Gly Met Ala Ile Leu Thr Ala Pro Trp
        115                 120                 125

Phe Leu Ala Glu Ile Arg Gly Tyr Gly Tyr Val Tyr Asp Lys Leu Asp
    130                 135                 140
```

-continued

```
Glu Tyr Gly Tyr Phe Tyr Leu Phe Phe Ser Ile Ala Leu Phe Leu Leu
145                 150                 155                 160

Phe Ser Asp Phe Leu Ile Tyr Trp Ile His Arg Ala Leu His His Arg
                165                 170                 175

Trp Leu Tyr Ala Pro Leu His Lys Leu His His Lys Trp Ile Val Pro
            180                 185                 190

Thr Pro Tyr Ser Ser His Ala Phe His Tyr Leu Asp Gly Tyr Ser Gln
        195                 200                 205

Ser Leu Pro Tyr His Met Phe Pro Phe Phe Pro Leu Asn Lys Tyr
    210                 215                 220

Val Tyr Leu Leu Leu Phe Gly Ser Val Asn Tyr Trp Thr Val Leu Ile
225                 230                 235                 240

His Asp Gly Lys Tyr Phe Ser Asn Asn Ala Val Val Asn Gly Ala Ala
                245                 250                 255

His His Ala Ala His His Met Tyr Phe Asn Tyr Asn Tyr Gly Gln Phe
                260                 265                 270

Phe Thr Leu Phe Asp Arg Leu Cys Ser Ser Tyr Arg Gln Pro Asp Gln
            275                 280                 285

Glu Leu Phe Asp Ala Glu Leu Arg Asn Glu Lys Leu Gln Glu Gln Arg
    290                 295                 300

Ile Arg Phe Met Glu Thr Val Gln Tyr Thr Val Glu Gly Lys Asp Asp
305                 310                 315                 320

Arg Thr Tyr Ala Ser Lys Lys Asp Asn
                325

<210> SEQ ID NO 18
<211> LENGTH: 281
<212> TYPE: PRT
<213> ORGANISM: DWF7/STE1 (Arabidopsis)

<400> SEQUENCE: 18

Met Ala Ala Asp Asn Ala Tyr Leu Met Gln Phe Val Asp Glu Thr Ser
1               5                   10                  15

Phe Tyr Asn Arg Ile Val Leu Ser His Leu Pro Ala Asn Leu Trp
            20                  25                  30

Glu Pro Leu Pro His Phe Leu Gln Thr Trp Leu Arg Asn Tyr Leu Ala
        35                  40                  45

Gly Thr Leu Leu Tyr Phe Ile Ser Gly Phe Leu Trp Cys Phe Tyr Ile
    50                  55                  60

Tyr Tyr Leu Lys Ile Asn Val Tyr Leu Pro Lys Asp Ala Ile Pro Thr
65                  70                  75                  80

Ile Lys Ala Met Arg Leu Gln Met Phe Ala Met Lys Ala Met Pro
                85                  90                  95

Trp Tyr Thr Leu Leu Pro Thr Val Ser Glu Ser Met Ile Glu Arg Gly
            100                 105                 110

Trp Thr Lys Cys Phe Ala Ser Ile Asp Glu Phe Gly Trp Ile Leu Tyr
        115                 120                 125

Phe Val Tyr Ile Ala Ile Tyr Leu Val Phe Val Glu Phe Gly Ile Tyr
    130                 135                 140

Trp Met His Arg Glu Leu His Asp Ile Lys Pro Leu Tyr Lys Tyr Leu
145                 150                 155                 160

His Ala Thr His His Ile Tyr Asn Lys Gln Asn Thr Leu Ser Pro Phe
                165                 170                 175

Ala Gly Leu Ala Phe His Pro Val Asp Gly Ile Leu Gln Ala Val Pro
```

-continued

```
                180                 185                 190
His Val Ile Ala Leu Phe Ile Val Pro Ile His Phe Thr Thr His Ile
            195                 200                 205
Gly Leu Leu Phe Met Glu Ala Ile Trp Thr Ala Asn Ile His Asp Cys
        210                 215                 220
Ile His Gly Asn Ile Trp Pro Val Met Gly Ala Gly Tyr His Thr Ile
225                 230                 235                 240
His His Thr Thr Tyr Lys His Asn Tyr Gly His Tyr Thr Ile Trp Met
                245                 250                 255
Asp Trp Met Phe Gly Ser Leu Arg Asp Pro Leu Leu Glu Glu Asp Asp
            260                 265                 270
Asn Lys Asp Ser Phe Lys Lys Ala Glu
        275                 280

<210> SEQ ID NO 19
<211> LENGTH: 291
<212> TYPE: PRT
<213> ORGANISM: delta-7 sterol C-5 desaturase concensus

<400> SEQUENCE: 19

Met Asp Leu Val Leu Glu Ala Asp His Tyr Val Phe Asp Asp Tyr Ala
1               5                   10                  15
Lys Ile Pro Leu Ala Ile Asp Ser Leu Leu Asn Val Ser Asn Ser Thr
            20                  25                  30
Leu Glu Thr Leu Asn Lys Val Asn Tyr Gly Pro Phe Leu Phe Asp Phe
        35                  40                  45
Thr Glu Thr Ser Phe Ser Leu Leu Pro Arg Asn Asn Leu Trp Arg Glu
    50                  55                  60
Phe Leu Ser Leu Trp Leu Ile Val Thr Ile Phe Gly Leu Leu Tyr Ile
65                  70                  75                  80
Ala Ser Leu Ser Tyr Phe Phe Asp Ile Phe Asn His Pro Lys Tyr Leu
                85                  90                  95
Lys Asn Gln Met Leu Glu Ile Lys Ala Val Ala Ile Pro Trp Met Ser
            100                 105                 110
Leu Leu Thr Val Pro Trp Phe Met Glu Leu Gly Tyr Ser Lys Leu Tyr
        115                 120                 125
Lys Ile Asp Glu His Gly Arg Lys Leu Phe Ile Glu Ala Thr Phe Phe
    130                 135                 140
Phe Thr Asp Gly Ile Tyr Ala His Arg Trp Leu His Trp Pro Tyr Lys
145                 150                 155                 160
Ala Leu His Lys Pro His His Lys Trp Leu Val Cys Thr Pro Phe Ala
                165                 170                 175
Ser His Ala Phe His Pro Val Asp Gly Tyr Leu Gln Ser Leu Tyr His
            180                 185                 190
Ile Tyr Pro Leu Leu Pro Leu His Lys Ser Tyr Leu Leu Phe Thr Phe
        195                 200                 205
Val Asn Phe Trp Thr Val Met Ile His Asp Gly Gln Ser Asn Asn Pro
    210                 215                 220
Val Val Asn Gly Ala Cys His Thr Val His His Leu Tyr Phe Asn Tyr
225                 230                 235                 240
Asn Tyr Gly Gln Phe Thr Thr Leu Trp Asp Arg Leu Gly Gly Ser Tyr
                245                 250                 255
Arg Arg Pro Asp Ser Leu Phe Asp Pro Lys Leu Arg Asp Lys Lys Glu
            260                 265                 270
```

-continued

```
Gln Arg Glu Thr Tyr Ile Glu Val Glu Gly Asp Asp Arg Tyr Asp
    275                 280                 285

Lys Lys Asn
    290
```

<210> SEQ ID NO 20
<211> LENGTH: 1889
<212> TYPE: DNA
<213> ORGANISM: Genomic dwf7 (Arabidopsis)

<400> SEQUENCE: 20

| | |
|---|---|
| gaagatcgat caatcaatca tcaaactctc tgtgtgccac atgcattact actgttgact | 60 |
| tgttcaataa aggtaaagta agatcaatcc ggcgaatctt ctttcgtttt ccggcaccga | 120 |
| tctcggtgga tctccgattc acatggcggc ggataatgct tatctgatgc agtttgttga | 180 |
| cgaaacctct ttttacaacc gaatcgttct gagtcatctt ttgccggcga atctatggga | 240 |
| acccttacct cattttctcc agacatggct ccgaaattac ctcgccggaa ccctactata | 300 |
| cttcatctcc ggtttcctct ggtgcttcta catctattac cttaaaatca cgtttacct | 360 |
| tcccaaaggt ctcgactttc acttttgtat tcactattgc ttaatcgctt tctatgttat | 420 |
| cgattttca atttaaggaa gagggttct tcgtgtactg tacagtaatt tggatttgat | 480 |
| gtggatagtt catgtttgca tttattgatt atttgtgcat attctccatc taagggattg | 540 |
| aacagttagt ggcttatata agttttgtg caaccaatga aagtcgtac atctttgaag | 600 |
| ttgaatttc tacttgccat ttaagtccac ttaaattgtt tgttgaagtg attgtctact | 660 |
| ttcagacaca ttctttttct gcttctctga gactctgtct tagtttgaaa tctttttgg | 720 |
| tctgttttgc ttcagatgca attcctacaa taaaggctat gcgtttgcaa atgtttgtgg | 780 |
| caatgaaggc tatgccatgg tacactcttc ttccaactgt ctccgagagt atgattgaac | 840 |
| gtggttggac caaatgtttt gctagcatag acgaattcgg ctggattctg tattttgttt | 900 |
| acatcgccat ctatcttgtt ttcgttgagt ttggtattta ttggatgcac agagagcttc | 960 |
| atgacattaa gcctctctat aagtatctcc atgccaccca tcatatctac aacaagcaga | 1020 |
| atacactctc tccatttgcc ggtaagtgtt ttcagtttgt tcttctttag ttcttgtaaa | 1080 |
| agattggtag catttagttt cttaccagaa aagactttgt cagcagctgc ttgtactcca | 1140 |
| aatcacattt tgcattcctt atccataaag taaccagaaa ggctagaatt atataaatgt | 1200 |
| cagctgcatt acttcacata tgtcagagag acttctgact taaccagagt ttagatcttt | 1260 |
| gtgtttctct tctggtctcg gactgattgg aaatgacgag aagttctttt atctacttcc | 1320 |
| ctggagtgta tcttggttaa tccaaggatg tgacatctaa tattacttgt aacttcctta | 1380 |
| cgttttgtt tacagggctt gcatttcacc cagtagacgg gatacttcag gctgtaccgc | 1440 |
| atgtgatagc gctgtttata gtgccaattc atttcacaac tcatataggt cttttgttca | 1500 |
| tggaagcgat atggacggcg aacatccatg actgcatcca tggcaacatc tggccagtaa | 1560 |
| tgggtgcagg ataccatacg ataccaccac cgacatacaa gcataactat ggtcattata | 1620 |
| ccatatggg ggattggatg tttggctctc ttagggatcc tctcttagaa gaagatgaca | 1680 |
| acaaagacag cttcaagaaa gcagagtgag aatgcccact tgggttttgt tcttctgttt | 1740 |
| tgtcttgtgt tgttgttgtt caaagtttca gcctttcttg ttcttttct tcttcttctt | 1800 |
| attcatgtgt ctctctcaac ctttccaatt atattgttac aaacatttgc tgtctagttt | 1860 |
| aaaacatgta aatgtttgat gatctttgc | 1889 |

<210> SEQ ID NO 21
<211> LENGTH: 281
<212> TYPE: PRT
<213> ORGANISM: DWF7

<400> SEQUENCE: 21

```
Met Ala Ala Asp Asn Ala Tyr Leu Met Gln Phe Val Asp Glu Thr Ser
  1               5                  10                  15

Phe Tyr Asn Arg Ile Val Leu Ser His Leu Leu Pro Ala Asn Leu Trp
             20                  25                  30

Glu Pro Leu Pro His Phe Leu Gln Thr Trp Leu Arg Asn Tyr Leu Ala
         35                  40                  45

Gly Thr Leu Leu Tyr Phe Ile Ser Gly Phe Leu Trp Cys Phe Tyr Ile
     50                  55                  60

Tyr Tyr Leu Lys Ile Asn Val Tyr Leu Pro Lys Asp Ala Ile Pro Thr
 65                  70                  75                  80

Ile Lys Ala Met Arg Leu Gln Met Phe Val Ala Met Lys Ala Met Pro
                 85                  90                  95

Trp Tyr Thr Leu Leu Pro Thr Val Ser Glu Ser Met Ile Glu Arg Gly
            100                 105                 110

Trp Thr Lys Cys Phe Ala Ser Ile Asp Glu Phe Gly Trp Ile Leu Tyr
        115                 120                 125

Phe Val Tyr Ile Ala Ile Tyr Leu Val Phe Val Glu Phe Gly Ile Tyr
    130                 135                 140

Trp Met His Arg Glu Leu His Asp Ile Lys Pro Leu Tyr Lys Tyr Leu
145                 150                 155                 160

His Ala Thr His His Ile Tyr Asn Lys Gln Asn Thr Leu Ser Pro Phe
                165                 170                 175

Ala Gly Leu Ala Phe His Pro Val Asp Gly Ile Leu Gln Ala Val Pro
            180                 185                 190

His Val Ile Ala Leu Phe Ile Val Pro Ile His Phe Thr Thr His Ile
        195                 200                 205

Gly Leu Leu Phe Met Glu Ala Ile Trp Thr Ala Asn Ile His Asp Cys
    210                 215                 220

Ile His Gly Asn Ile Trp Pro Val Met Gly Ala Gly Tyr His Thr Ile
225                 230                 235                 240

His His Thr Thr Tyr Lys His Asn Tyr Gly His Tyr Thr Ile Trp Met
                245                 250                 255

Asp Trp Met Phe Gly Ser Leu Arg Asp Pro Leu Leu Glu Glu Asp Asp
            260                 265                 270

Asn Lys Asp Ser Phe Lys Lys Ala Glu
        275                 280
```

<210> SEQ ID NO 22
<211> LENGTH: 2925
<212> TYPE: DNA
<213> ORGANISM: Genomic HDF7

<400> SEQUENCE: 22

```
gtttggtatt tattggatgc acagagagct tcatgacatt aagcctctct ataagtatct      60
ccatgccacc catcatatct acaacaagca gaatacactc tctccatttg ccggtaagtg     120
ttttcagttt gttcttcttt agttcttgta aaagattggt agcatttagt ttcttaccag     180
aaaagacttt gtcagcagct gcttgtactc caaatcacat tttgcattcc ttatccataa     240
agtaaccaga aaggctagaa ttatataaat gtcagctgca ttacttcaca tatgtcagag     300
```

```
agacttctga cttaaccaga gtttagatct ttgtgtttct cttctggtct cggactgatt    360
ggaaatgacg agaagttctt ttatctactt ccctggagtg tatcttggtt aatccaagga    420
tgtgacatct aaatattact tgtaacttcc ttacgttttt gtttacaggg cttgcattca    480
cccagtagac gggatactta aggctgtacc gcatgtgata gcgctgttat agtgccaatt    540
catttcacaa ctcatatagg tcttttgttc atggaagcga tatggacggc gaacatccat    600
gactgcatcc atggcaacat ctggccagta atgggtgcag ataccatac gatacaccac     660 acgacataca agcataacta tggtcattat accatatgga tggattggat gtttggctct    720
cttagggatc ctctcttaga agaagatgac aacaaagaca gcttcaagaa agcagagtga    780
gaatgcccac ttgggttttg ttcttctgtt ttgtcttgtg ttgttgttgt tcaaagtttc    840
agcctttctt gttcttttc ttcttcttct tattcatgtg tctctctcaa cctttccaat     900
tatattgtta caaacatttg ctgtctagtt taaaacatgt aaatgtttga tgatctttgc    960
aagactccat ttttgtttaa ggtaaacctt gaatctcata gattgtcgat tgttggtatt   1020
tccattttca ggtacggttc tgtagactgt agtcttgctg accagtccgg cttaaccacc   1080
ccaaatttca aagatctcac caatcaaaat gctggctggc cccaatatat agatgggcca   1140
gttaatccgt ctagctttac tctttagacc taccttagac agttagacac ctgctaatta   1200
atgagtttcc ttttcttgt tcagcaagtt acctgtgtta cttgagagtt gagttaatgg    1260
tagtaaacgc aatttaaccc ttataagttt aatcgtattc aacgaatgac ccagagactt   1320
taaataaatc catcgtaacc ctccacttca aaattctttt taaaaagtag caaatcattt   1380
aaatattgta agtttgcttc attcgaaatt gtagctacag atctcaaagc tcctcctgtt   1440
ggccatatct ctctctaaca aacgcatagt aacacttgac cacagtttga cttctcggcg   1500
gtttcatggc ggcgactatg gcagattata atgatcagat cgtcaatgag acctcttttt   1560
acaaccgaat ggttctgagt cacctttgc cggtgaatct atgggaacct ttaccacatt    1620
tcctccagac atggctccgg aactacctcg ccggaaacat actctacttc atctccggct   1680
tcctctggtg cttctacatc tattaccta aactcaacgt ttacgtcccc aaaggttact    1740
tttttcaatt tcgatgttct gttttgaaac ctttcttttg ttgattcctt cgattgtatc   1800
gcctgataga ttgtgttata cgttaaccct ttttcttac tgttactttc agttcttgtc    1860
ttctacttct catttaatta gttttaaagt ttaatatttt tggctaatcc acattttta    1920 agttgaatct tccatgaaat ttgagctcaa aatataccat gaaattgaaa tttgtggttc   1980
ttagttctat ttcttgcttg gtttcttcta tttttgtggt tagaatccat tcctacgaga   2040
aaggcaatgc ttttgcaaat atacgtggca atgaaggcta tgccttggta cactcttctt   2100
ccagctgtct ctgagtatat gatcgagcat ggttggacca aatgttactc tacacttgac   2160
catttcaact ggttcctctg tttcctctac atagctctct atcttgtttt agttgagttt   2220
atgatttatt gggttcacaa agagcttcat gacattaaat ttctctataa gcatctccat   2280
gctacccatc atatgtacaa caagcaaaac acactctctc catttgccgg tatgtcaaag   2340
ctatatgttc tcaatctaaa ttcaagagct tgtatcaatg gtgacttctt tacttgatgt   2400
ttttcgggtt ttcagggctc gcattccatc cgctggacgg atacttcag gctataccgc    2460 acgtgatagc gctgtttata gtgccgattc atctcataac acatctgagt cttttgtttt   2520
tggaagggat atggacagca agcatccatg attgcataca tggtaacatc tggcctataa   2580
tgggtgcagg ataccatacc atacaccata aacatacaa gcataactat ggtcattata    2640
ccatatggat ggactggatg tttggctctc ttatggttcc tttagcagaa aaagacagtt   2700
```

-continued

```
tcaaggagaa agaaaagtga gaatgttcaa tgctcacatg tattcttcat atgttgctct    2760
tctcgtgact cttattaaaa cctttctaat cactttggtg gaattaaaaa catgactgca    2820
taatttgatg caaagtttca gactttttatt gctaaaaatc tctgatgatt attaacctca   2880
attatataat tgctggatga agagttcaaa tttggactaa atctg                    2925
```

<210> SEQ ID NO 23
<211> LENGTH: 279
<212> TYPE: PRT
<213> ORGANISM: HDF7

<400> SEQUENCE: 23

```
Met Ala Ala Thr Met Ala Asp Tyr Asn Asp Gln Ile Val Asn Glu Thr
 1               5                  10                  15

Ser Phe Tyr Asn Arg Met Val Leu Ser His Leu Leu Pro Val Asn Leu
                20                  25                  30

Trp Glu Pro Leu Pro His Phe Leu Gln Thr Trp Leu Arg Asn Tyr Leu
            35                  40                  45

Ala Gly Asn Ile Leu Tyr Phe Ile Ser Gly Phe Leu Trp Cys Phe Tyr
        50                  55                  60

Ile Tyr Tyr Leu Lys Leu Asn Val Tyr Val Pro Lys Glu Ser Ile Pro
 65                  70                  75                  80

Thr Arg Lys Ala Met Leu Leu Gln Ile Tyr Val Ala Met Lys Ala Met
                85                  90                  95

Pro Trp Tyr Thr Leu Leu Pro Ala Val Ser Glu Tyr Met Ile Glu His
            100                 105                 110

Gly Trp Thr Lys Cys Tyr Ser Thr Leu Asp His Phe Asn Trp Phe Leu
        115                 120                 125

Cys Phe Leu Tyr Ile Ala Leu Tyr Leu Val Leu Val Glu Phe Met Ile
    130                 135                 140

Tyr Trp Val His Lys Glu Leu His Asp Ile Lys Phe Leu Tyr Lys His
145                 150                 155                 160

Leu His Ala Thr His Met Tyr Asn Lys Gln Asn Thr Leu Ser Pro
                165                 170                 175

Phe Ala Gly Leu Ala Phe His Pro Leu Asp Gly Ile Leu Gln Ala Ile
            180                 185                 190

Pro His Val Ile Ala Leu Phe Ile Val Pro Ile His Leu Ile Thr His
        195                 200                 205

Leu Ser Leu Leu Phe Leu Glu Gly Ile Trp Thr Ala Ser Ile His Asp
    210                 215                 220

Cys Ile His Gly Asn Ile Trp Pro Ile Met Gly Ala Gly Tyr His Thr
225                 230                 235                 240

Ile His His Thr Thr Tyr Lys His Asn Tyr Gly His Tyr Thr Ile Trp
                245                 250                 255

Met Asp Trp Met Phe Gly Ser Leu Met Val Pro Leu Ala Glu Lys Asp
            260                 265                 270

Ser Phe Lys Glu Lys Glu Lys
        275
```

<210> SEQ ID NO 24
<211> LENGTH: 60
<212> TYPE: PRT
<213> ORGANISM: dwf7-2

<400> SEQUENCE: 24

-continued

```
Met Ala Ala Asp Asn Ala Tyr Leu Met Gln Phe Val Asp Glu Thr Ser
1               5                   10                  15

Phe Tyr Asn Arg Ile Val Leu Ser His Leu Leu Pro Ala Asn Leu Trp
            20                  25                  30

Glu Pro Leu Pro His Phe Leu Gln Thr Trp Leu Arg Asn Tyr Leu Ala
        35                  40                  45

Gly Thr Leu Leu Tyr Phe Ile Ser Gly Phe Leu Trp
    50                  55                  60
```

<210> SEQ ID NO 25
<211> LENGTH: 230
<212> TYPE: PRT
<213> ORGANISM: dwf7-1

<400> SEQUENCE: 25

```
Met Ala Ala Asp Asn Ala Tyr Leu Met Gln Phe Val Asp Glu Thr Ser
1               5                   10                  15

Phe Tyr Asn Arg Ile Val Leu Ser His Leu Leu Pro Ala Asn Leu Trp
            20                  25                  30

Glu Pro Leu Pro His Phe Leu Gln Thr Trp Leu Arg Asn Tyr Leu Ala
        35                  40                  45

Gly Thr Leu Leu Tyr Phe Ile Ser Gly Phe Leu Trp Cys Phe Tyr Ile
    50                  55                  60

Tyr Tyr Leu Lys Ile Asn Val Tyr Leu Pro Lys Asp Ala Ile Pro Thr
65                  70                  75                  80

Ile Lys Ala Met Arg Leu Gln Met Phe Val Ala Met Lys Ala Met Pro
                85                  90                  95

Trp Tyr Thr Leu Leu Pro Thr Val Ser Glu Ser Met Ile Glu Arg Gly
                100                 105                 110

Trp Thr Lys Cys Phe Ala Ser Ile Asp Glu Phe Gly Trp Ile Leu Tyr
            115                 120                 125

Phe Val Tyr Ile Ala Ile Tyr Leu Val Phe Val Glu Phe Gly Ile Tyr
        130                 135                 140

Trp Met His Arg Glu Leu His Asp Ile Lys Pro Leu Tyr Lys Tyr Leu
145                 150                 155                 160

His Ala Thr His His Ile Tyr Asn Lys Gln Asn Thr Leu Ser Pro Phe
                165                 170                 175

Ala Gly Leu Ala Phe His Pro Val Asp Gly Ile Leu Gln Ala Val Pro
            180                 185                 190

His Val Ile Ala Leu Phe Ile Val Pro Ile His Phe Thr Thr His Ile
        195                 200                 205

Gly Leu Leu Phe Met Glu Ala Ile Trp Thr Ala Asn Ile His Asp Cys
    210                 215                 220

Ile His Gly Asn Ile Trp
225                 230
```